(12) United States Patent
Raman et al.

(10) Patent No.: US 10,624,601 B2
(45) Date of Patent: Apr. 21, 2020

(54) IMAGING PROTOCOL MANAGER PUSHING SYSTEMS AND METHODS

(71) Applicant: GENERAL ELECTRIC COMPANY, Schenectady, NY (US)

(72) Inventors: Balaji Raman, Menomonee Falls, WI (US); Nitin Mallya, Bangalore (IN); Adrian Knowles, Brookfield, WI (US)

(73) Assignee: General Electric Company, Schenectady, NY (US)

(*) Notice: Subject to any disclaimer, the term of this patent is extended or adjusted under 35 U.S.C. 154(b) by 351 days.

(21) Appl. No.: 15/821,397

(22) Filed: Nov. 22, 2017

(65) Prior Publication Data

US 2018/0144823 A1    May 24, 2018

Related U.S. Application Data

(60) Provisional application No. 62/426,076, filed on Nov. 23, 2016.

(51) Int. Cl.
*A61B 6/00* (2006.01)
*H04N 5/232* (2006.01)
(Continued)

(52) U.S. Cl.
CPC .............. *A61B 6/545* (2013.01); *A61B 5/055* (2013.01); *A61B 6/563* (2013.01); *A61B 6/566* (2013.01); *A61B 8/54* (2013.01); *A61B 8/565* (2013.01); *G06F 16/289* (2019.01); *G06F 16/951* (2019.01); *G16H 40/63* (2018.01);
(Continued)

(58) Field of Classification Search
CPC ......... A61B 6/545; A61B 5/055; A61B 6/563; A61B 6/566; A61B 8/54; A61B 8/565; G16H 40/67; G16H 40/63; G06F 16/289; G06F 16/951; H04L 67/02; H04L 67/12;
(Continued)

(56) References Cited

U.S. PATENT DOCUMENTS 9,020,849 B2    4/2015    Kasai et al.
2001/0018659 A1*   8/2001    Koritzinsky ......... A61B 5/0002
                                                                       705/3
(Continued)

OTHER PUBLICATIONS

Siemens, Make the power of teamplay your own, https://bps-healthcare.siemens.com/teamplay/en/core-apps, last accessed Nov. 22, 2017, 9 pages.

*Primary Examiner* — Wing F Chan
*Assistant Examiner* — Billy H Ng

(57) ABSTRACT

A cloud-based imaging protocol manager pushes standard imaging protocols from the cloud to imaging devices registered with the protocol manager. The protocol manager maintains a library storing standard imaging protocols, determines whether an imaging device is compatible with the standard protocol(s) to be pushed, creates a push command which requests pushing the standard protocol(s) to a compatible imaging device, stores the push command in a command queue, converts the standard protocol(s) to raw protocol(s) usable by the imaging device. The imaging device polls the command queue to receive the push command, downloads the raw protocol(s) from the protocol manager, commits or refuses to commit the downloaded protocol(s), and sends a notification to the protocol manager indicating execution status of the push command.

20 Claims, 23 Drawing Sheets

(51) Int. Cl.

| | | |
|---|---|---|
| *A61B 5/055* | (2006.01) | |
| *A61B 8/00* | (2006.01) | |
| *G06F 16/28* | (2019.01) | |
| *G06F 16/951* | (2019.01) | |
| *G16H 40/63* | (2018.01) | |
| *G16H 40/67* | (2018.01) | |
| *H04L 29/08* | (2006.01) | |
| *A61B 6/03* | (2006.01) | |
| *G16H 30/20* | (2018.01) | |
| *H04L 29/06* | (2006.01) | |

(52) U.S. Cl.
CPC .............. *G16H 40/67* (2018.01); *H04L 67/02* (2013.01); *H04L 67/12* (2013.01); *H04L 67/26* (2013.01); *H04L 67/32* (2013.01); *H04L 67/34* (2013.01); *H04N 5/23206* (2013.01); *A61B 6/032* (2013.01); *A61B 6/037* (2013.01); *G16H 30/20* (2018.01); *H04L 63/08* (2013.01); *H04L 67/10* (2013.01); *H04N 5/23225* (2013.01)

(58) Field of Classification Search
CPC ......... H04L 67/26; H04L 67/32; H04L 67/34; H04N 5/23206
See application file for complete search history.

(56) References Cited

U.S. PATENT DOCUMENTS

| | | | |
|---|---|---|---|
| 2005/0209888 A1* | 9/2005 | Oowaki | A61B 6/542 705/3 |
| 2007/0211756 A1* | 9/2007 | Glaser-Seidnitzer | A61B 5/055 370/466 |
| 2016/0148017 A1 | 5/2016 | Gossler et al. | |

* cited by examiner

IMAGING PROTOCOL MANAGER PUSHING SYSTEMS AND METHODS

CROSS REFERENCE TO RELATED APPLICATIONS

The present application claims the benefit of U.S. provisional application No. 62/426,076 filed Nov. 23, 2016, which is incorporated herein by reference. The present application relates to "Imaging Protocol Manager" (PCT/US17/63059) and "Imaging Protocol Manager Pulling Systems and Methods" (Ser. No. 15/821,198), which are filed on the same day as the present application and incorporated herein by reference.

FIELD

This disclosure relates to systems and methods for managing protocols for imaging devices.

BACKGROUND

Imaging devices (e.g., magnetic resonance (MR) scanner, computed tomography (CT) scanner, X-ray acquisition system, positron emission tomography (PET) scanner, nuclear medicine (NM) scanner, etc.) use imaging procedures to obtain image data of a target, such as a patient. An imaging procedure is associated with one or more imaging protocols that define image acquiring and/or processing actions or elements, such as one or more imaging parameters, one or more scanning planes in which image(s) are to be captured, and so on. For example, an imaging protocol may include parameters for an imaging device, such as tube current, tube voltage, filter usage, filter type, scan speed, etc. An imaging protocol may define a scanning plane for the associated imaging procedure, specify position and orientation of anatomical structure(s) or region(s) of interest in the patient, etc. An imaging protocol may further specify limits and/or other guidance on image noise, spatial resolution, and image texture including edge sharpness, artifacts, and radiation dose.

An imaging device maintains a protocol database which stores various imaging procedures and/or protocols for the device to use according to one or more scenarios, reasons for examination, etc. The scenarios for examination may include patient size, anatomy type (e.g., heart, lung, kidney, brain, etc.), position, task, etc. For example, imaging protocols can be constructed for particular clinical tasks. A task function such as tumor detection, tumor sizing, vessel sizing, etc., can be incorporated into an objective function to determine a dose distribution for a given task and to find a minimum possible dose for a given performance level. During protocol development, results from similar clinical tasks (e.g., tuning for a given anatomical location, etc.) can be used to inform initial parameter selection for another clinical task (e.g. bone imaging in the wrist may be used to inform the initial selection of parameters for bone imaging in the ankle, etc.).

Additionally, protocols for similar scenarios and tasks may vary on different brands/models of imaging devices. As an example, a protocol for a liver scan by imaging scanner A indicates a 120 kV tube current at 300 mA for 1 second. Scanner B of another model can rotate faster and uses a higher tube current to generate the same signal with a protocol of 120 kV at 400 mA for 0.75 second. As another example, a protocol for pediatric abdomen scan by scanner A indicates 80 kV, 200 mA, a helical pitch of 1, etc. Scanner B has a wider scan coverage such that a helical pitch can be translated to a single axial acquisition and thus uses a protocol of 70 kV, 300 mA, and axial at wide coverage. As another example, an imaging protocol for scanner A includes a first priority indicating a desired limit of radiation dose level and a second priority indicating a reduction of motion artifacts by using 80 kV at 200 mA for pediatric abdomen scan. If scanner B has lower kV capabilities, the protocol for scanner B may be adjusted to 70 kV at 300 mA. As another example, scanner A has a protocol for an inner ear scan which indicates 120 kV, 200 mA, and a bone kernel filter. Scanner B has a different kernel filter that can improve bone images compared to the bone kernel filter of Scanner A, but impacts the amount of signal that is required. Therefore, the impact may be accounted for such that the scanner B protocol includes 120 kV, 300 mA, and a "bone plus" kernel.

Imaging procedure and associated imaging protocol(s) can be visualized via a graphical user interface (GUI) for a user (e.g., radiologist, technician, clinical specialist) to select. For example, an interactive user interface can include menu and control options to allow the user to select and configure an imaging protocol. For an X-ray imaging protocol for example, the interface allows the user to select an acquisition trajectory, manage radiation dose in real-time, control tube angular orientation, tube tilt, tube position, table motion and/or orientation and other parameters for imaging during reference and/or tomosynthesis scans. When the user selects the imaging protocol via the interface, an imaging procedure associated with the imaging protocol will be performed.

For an organization (e.g., hospital, clinic) that has a large fleet of imaging devices at various facilities, managing protocols for the devices can be very costly and time-consuming. Exam quality may be inconsistent due to inconsistent protocols used across the facilities, which may put patient safety and outcome at risk. Compliance with regulations and accreditation requirements may be challenging due to variability in dose, exam duration, and diagnostics quality. In addition, protocols need to be reviewed and kept current all the time. However, modification of protocols may be inefficient because protocols are modified per exam, which results in loss of productivity and revenue. An imaging protocol management system and method with improved efficiency and outcome are generally desired.

BRIEF SUMMARY

In one embodiment, the present disclosure provides a cloud-based imaging protocol manager leveraging one or more processors and one or more storage devices in a cloud. The imaging protocol manager comprises a library storing standard imaging protocols, and a compatibility checker configured to determine one or more compatible imaging devices from a plurality of imaging devices registered with the imaging protocol manager that are compatible with one or more standard imaging protocols of the library. The imaging protocol manager also comprises an orchestrator configured to create a push command which requests pushing the one or more standard imaging protocols to a particular imaging device of the one or more compatible imaging devices, and a command queue storing the push command. The particular imaging device polls the command queue to receive the push command. The imaging protocol manager further comprises a push enricher configured to convert the one or more standard imaging protocols to one or more raw protocols in a format used by the particular imaging device, a data store storing the one or more raw protocols for the particular imaging device to download, and a notification queue storing a notification from the particular imaging device. The notification indicates execution status of the push command.

In another embodiment, the present disclosure provides an apparatus comprising a cloud agent in communication with a cloud-based imaging protocol manager. The cloud agent is configured to poll the imaging protocol manager and receive a push command from the imaging protocol manager. The push command requests pushing one or more imaging protocols to an imaging device registered with the imaging protocol manager. The cloud agent is also configured to download the one or more imaging protocols associated with the push command from the imaging protocol manager and notify a user of the push command. The cloud agent is further configured to commit or refuse to commit the one or more imaging protocols to a protocol database of the imaging device based on a user input; and send a notification indicating execution status of the push command to the imaging protocol manager.

In another embodiment, the present disclosure provides a method performed by an imaging protocol manager in a cloud for pushing imaging protocols from the cloud to imaging devices. The method comprises storing standard imaging protocols in the cloud and determining one or more compatible imaging devices from a plurality of imaging devices registered with the imaging protocol manager that are compatible with one or more standard imaging protocols of the library. The method also comprises creating a push command which requests pushing the one or more standard imaging protocols to a particular imaging device of the one or more compatible imaging devices, and storing the push command in a command queue. The particular imaging device polls the command queue to receive the push command. The method further comprises converting the one or more standard imaging protocols to one or more raw protocols in a format used by the particular imaging device, storing the one or more raw protocols for the particular imaging device to download, and receiving a notification from the particular imaging device. The notification indicates execution status of the push command.

In yet another embodiment, the present disclosure provides a method performed by an apparatus in communication with an imaging protocol manager in a cloud for pushing imaging protocols from the cloud to an imaging device registered with the imaging protocol manager. The method comprises polling the imaging protocol manager and receiving a push command from the imaging protocol manager. The push command requests pushing one or more imaging protocols to the imaging device. The method also comprises downloading the one or more imaging protocols associated with the push command from the imaging protocol manager, and notifying a user of the push command. The method further comprises committing or refusing to commit the one or more imaging protocols to a protocol database of the imaging device based on a user input, and sending a notification indicating execution status of the push command to the imaging protocol manager.

BRIEF DESCRIPTION OF THE DRAWINGS

Various aspects of this disclosure may be better understood upon reading the following detailed description and upon reference to the drawings in which.

Figure 1:
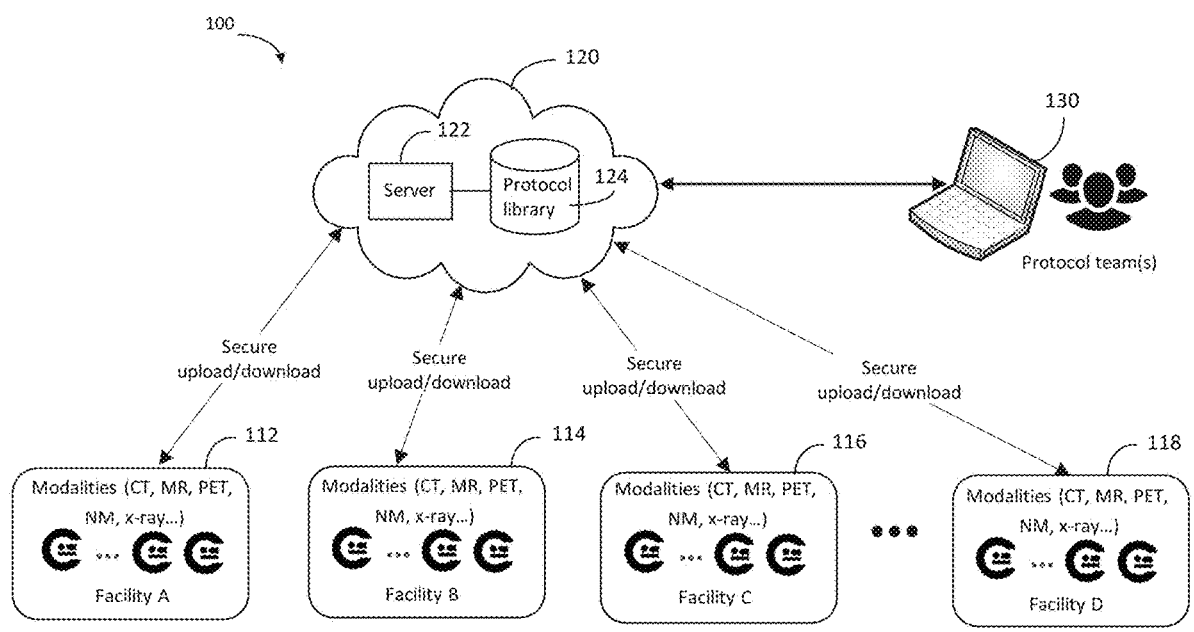
FIG. 1 is a schematic diagram of a system in which an imaging protocol manager is used, in accordance with an exemplary embodiment.

The drawings illustrate specific aspects of the described components, systems and methods for providing phototherapy treatment. Together with the following description, the drawings demonstrate and explain the principles of the structures, methods, and principles described herein. In the drawings, the thickness and size of components may be exaggerated or otherwise modified for clarity. Well-known structures, materials, or operations are not shown or described in detail to avoid obscuring aspects of the described components, systems and methods.

DETAILED DESCRIPTION

One or more specific embodiments of the present disclosure are described below in order to provide a thorough understanding. These described embodiments are only examples of the systems and methods for managing imaging protocols. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

In addition, it should be understood that references to "one embodiment" or "an embodiment" of the present disclosure are not intended to be interpreted as excluding the existence of additional embodiments that also incorporate the recited features.

Referring to the figures generally, the present disclosure is to provide systems and methods for managing imaging protocols for a fleet of imaging devices. An example imaging protocol managing system includes a cloud-based protocol manager that manages imaging protocols across multiple modalities. Imaging devices are registered with the protocol manager first. The protocol manager then automatically communicates with the registered devices and imports (i.e., pulls) protocols from the devices to save in the cloud. Protocol team(s) such as radiologist, technicians, clinicians, and researchers, can access the protocol manager from a computing device (e.g., workstation, computer, laptop), viewing and editing the protocols pulled from the devices. The protocol team can mark some protocols as "standard" protocols, which are published in a protocol library at the cloud. The protocol manager can distribute (i.e., push) the standard protocols in the library to applicable imaging devices in the fleet. The protocol manager also tracks and monitors deviation between protocols used by devices and standard protocols in the cloud library.

Via the cloud-based library, the protocol manager facilitates remote pull and push of protocols, which eliminates the need for manually updating protocols on a plurality of imaging devices and thereby eliminating significant time waste. In this way, the protocol manager helps healthcare providers deliver right imaging protocols for each patient with consistency and accuracy over time, which satisfies regulatory and accreditation requirements and governance for imaging protocols. Thus, variability in protocols and image quality can be reduced, patient safety and consistency of care can be improved. Operational efficiency can be improved by standardizing workflow and procedures across multiple facilities and locations via a centralized protocol library. An effective protocol management process can be established using the protocol manager, insights, and education across the enterprise.

Example Definitions

In certain examples, web services, such as Amazon Web Services (AWS), refer to a secure cloud services platform providing compute power, database storage, content delivery and other functionality.

An approved protocol is a protocol that has been reviewed and signed-off by the appropriate stakeholders.

Clinical instructions are instructions regarding exam completion other than technical settings for the exam. Clinical instructions can include positioning information, example images, patient preparation instructions, oral contrast instructions, injected contrast and injector settings, etc.

A deviation is a difference between a protocol stored on a specific device and a corresponding published protocol stored within a protocol manager library on the cloud.

A device is a physical asset in a physical location.

A facility is a single physical location at which a device is located. A facility may also be called a site.

A master protocol is a container that holds clinical instructions and technical settings for a single clinical indication. A master protocol can hold many sets of technical settings for different device models.

Microservices is a specialization of, and implementation approach, for service-oriented architectures (SOA) used to build flexible, independently deployable software systems. Microservices are typically lightweight and smaller in granularity than typical SOAs.

A model is a unique device type or platform for which technical settings are constructed. A model is also referred to as a type. A protocol can include multiple sets of technical settings for different models of devices.

A protocol, as described above, is a description of an imaging exam that includes technical settings. In some occasions, a protocol is used to refer to a combination of technical setting, clinical instructions, and notes. A protocol can also be referred to as an imaging protocol.

Performed protocols are protocols that include actual parameters used by a technologist during an exam.

Planned protocols are site protocols in the device library or cloud library for a particular equipment model. Planned protocols are protocols that are used at the device for scanning patients based on a clinical indication.

A published protocol is a protocol that has been distributed or scheduled to be distributed from a protocol manager to one or more devices. A user intends the published protocol to be used as-is by the operators at each facility. Protocols must be approved prior to being published. Once published, deviations are measured as differences between what is stored on a device and the published protocol.

A reconstruction is a specific set of instructions regarding how an imaging series (e.g., computed tomography (CT), magnetic resonance (MR), x-ray, ultrasound, etc.) is to be reconstructed into images. A single series (e.g., CT, MR, x-ray, ultrasound, etc.) can have multiple reconstructions.

A series is a lowest-level building block for a protocol. A series includes a scan, reconstruction, and reformatting/viewing settings. A series can be used in multiple protocols, for example.

A site is a single physical location at which a device is located, otherwise known as a facility.

Technical settings are device settings including acquisition parameters, reconstructions, reformatting, etc.

A type is a device model or platform for which technical settings are constructed. A type is also referred to as a model. A protocol can include multiple sets of technical settings for different types of devices, for example.

A version is a single form of a protocol captured at a point in time. Protocol versions are identified by a number and the date on which they were created, for example.

Example Imaging Protocol Manager Systems and Methods

An imaging protocol management system includes a cloud-based multi-modality protocol manager that helps identify protocol variation, standardize imaging workflow, and improve protocol compliance to achieve patient safety, operational efficiency, and optimize patient experience, for example. Prior solutions subjected customers to inconsistent exam quality and patient experience across facilities, resulting in loss of productivity (e.g., repeated exams, etc.), referrals, and challenges in meeting regulatory and accreditation requirements, for example. Instead, certain examples disclosed herein provide a cloud-based protocol management system that helps providers deliver the right image for each patient with consistency and accuracy over time, while satisfying regulatory and accreditation requirements and governance for protocols on imaging devices.

For example, patient outcomes can be improved by reducing variability in protocols and image quality to improve patient safety and consistency of care. Certain examples manage compliance by meeting protocol management regulatory and industry guidelines, as well as improve compliance with clinical standards. Operational efficiency can be improved by standardizing workflow/procedures across multiple facilities and locations via a centralized protocol library, for example. Certain examples facilitate culture change by establishing an effective protocol management process using a protocol manager, insights, and education across the enterprise.

In certain examples, protocols can be automatically pulled into a library, and the protocols library can be organized and managed by filtering, comparing, setting a gold standard, reviewing deviation, viewing history, tagging, and/or commenting, for example. Via the cloud-based library, certain examples facilitate remote push-pull of protocols, which helps eliminate a need for customers such as a physicist of lead technician to physically update protocols on a plurality of scanners. Rather, centralized protocol management with edit support (e.g., protocol renaming, etc.) helps to eliminate significant time waste. Certain examples enable analytics and editing via a "smart" cloud which removes a need for on-scanner protocol development. Instead, users are provided with natural language advice regarding desired protocols and/or parameters leveraging site and community protocols, predictive analytics, machine learning techniques, etc. Certain examples enable community collaboration by enabling users to search, learn, and share expertise with other community members.

In certain examples, a user and/or health organization (e.g., a hospital, clinic, hospital network, etc.) can register for cloud-based access and/or other access to an imaging protocol manager. For example, an email invitation can be sent to a user who can register and create a website for access to the protocol manager via the cloud. Imaging devices, such as CT scanners, MR systems, x-ray devices, etc., can be added to the protocol manager system. When a device is added, the imaging protocol manager automatically communicates with the device to pull information from the imaging device such as software information (e.g., version, parameters, etc.) and activate the imaging device to import imaging protocol information from the device.

The imaging protocol manager analyzes the imaging protocols obtained from the imaging device (e.g., pulled from the device and stored in a cloud-based data store for the imaging protocol manager, etc.). A particular imaging protocol can be accessed for reviewing and/or editing. In certain examples, a "standard" protocol in the library protocol and a device protocol can be compared to determine whether the device protocol deviates from the standard library protocol. The library protocol can be kept or overridden (e.g., replaced, etc.) by the device protocol. If the library protocol is replaced/updated by the protocol pulled from the imaging device, the device protocol can be designated as a standard library protocol and/or an imaging device-specific protocol for a certain type, subset, etc., of imaging device, for example. The standard protocol can be pushed from the library to one or more applicable imaging devices, for example.

In certain examples, a user can review a list of protocols via a graphical user interface (GUI). For example, the GUI can provide a view of devices running a protocol, and a user can see which device/protocol is deviating (e.g., via a graphical indication of deviation to catch the user's attention, deviation status, etc.). The user can click on or otherwise select a protocol and/or associated device in the list to view difference(s) between the device protocol and the standard library protocol (e.g., which parameter type(s), value(s), etc., is/are different, etc.). The user can then specify whether to use the device protocol or the library protocol, for example. In certain examples, standard protocols are organized in one or more libraries in the cloud system. Each library can have one or more groups, subgroups, etc., organized by device, device type, imaging type, location, organization, etc. In certain example, the GUI can show a view of connected device(s) and protocol deviation(s), and other information, such as status of pulling/pushing transactions, notifications, help information, etc.

In certain examples, an imaging protocol includes and/or is coupled, paired, combined, and/or otherwise associated with clinical instructions. Clinical instructions indicate what is to be done to perform a scan according to a certain imaging protocol including parameters, how to scan, what to do with the patient, etc. The protocol also includes technical settings which instruct an imaging device to be configured to scan the patient. Protocols and associated clinical instructions and technical settings can be pulled from devices, stored in a data store, analyzed, and pushed to devices via the protocol manager, for example.

Thus, certain examples facilitate automated rules management that does not rely on a customer for baselining. A user runs a baselining via the cloud-based imaging protocol manager system to improve process standardization through rules management. Via the protocol manager, a protocol name can be changed, protocols can be numbered, anatomical region can be changed, etc. A comparison view can compare protocols, versions of protocol, etc.

In certain examples, the protocol manager provides a staging area. The staging area provides a temporary workspace to modify and/or review an imaging protocol from an imaging device before sending the protocol to a library in the cloud-based protocol manager storage. A protocol can be stored in connection with a device and/or type of imaging device, for example. In certain examples, a protocol can be translated across imaging device models, etc.

Certain examples provide a plurality of methods and/or mechanisms to connect imaging devices to a cloud-based image protocol manager. For example, two methods can be provided to connect older and/or newer imaging devices to the imaging protocol manager. Some devices (e.g., newer CT scanners, etc.) can include a cloud agent on the devices that can directly talk to the image protocol manager cloud. Some devices (e.g., older CT scanners, etc.) can leverage a back-office network that communicates with the devices, and the back-office network includes a cloud agent. The cloud agent communicates with the devices to obtain imaging protocol(s) and then communicates with the cloud-based imaging protocol manager via the back-office network. Thus, certain examples provide direct communication between an imaging device and the cloud-based protocol manager, and other examples provide a back-office intermediary for network communications.

An example process includes first registering and then activating an imaging device. Once the device is activated, protocol(s) can be pulled from the device. Protocol(s) on a selected device can be reviewed, and baselining is performed to identify protocol(s) deviating from the available library(-ies). If a deviation is identified, then the deviating protocol is reviewed to determine whether the deviating protocol is to be committed to the library or should be discarded/replaced by the library version.

As will be described further below, certain examples can integrate with and operate in a variety of healthcare environments and impact a variety of healthcare scenarios and data through sensing, decision support, workflow management, and control. The following section provides some context and example environment for the presently disclosed technology described further in the subsequent section below.

Referring to FIG. 1, a schematic diagram of a system 100 where an imaging protocol manager is used is shown, in accordance with certain examples. As illustrated in FIG. 1, the system 100 includes a plurality of scanning devices 112, 114, 116, and 118 of various modalities (e.g., CT, MR, PET, NM, X-ray, etc.) located at various facilities A, B, C, and D. In some examples, the facilities A, B, C, and D are operated by one organization (e.g., hospital, clinic). A cloud-based imaging protocol manager 120 leverages one or more server 122 and one or more database 124 connected by network (i.e., in the cloud). A protocol library is stored in the database 124. Structure of the imaging protocol manager 120 will be discussed below in detail with reference to FIGS. 2 and 3.

Imaging devices 112-118 are communicably connected to the imaging protocol manager 120 via network. Communication between the imaging devices 112-118 and the protocol manager 120 is secure. In some examples, one or more of the imaging devices 112-118 are connected directly to the cloud. In particular, a cloud agent (e.g., client-side application) runs on an imaging device and talks to the protocol manager (e.g., a server-side application) in the cloud. In some examples, one or more of the imaging devices 112-118 are connected to the cloud via a back-office network (e.g., an edge services platform, Internet of things (IoTs) platform, etc.). The back-office network runs the cloud agent and facilitates communication between the imaging device and the cloud. In some embodiments, one or more of the imaging devices 112-118 are connected to the cloud through a virtual private network (VPN) tunneling. An imaging device runs the cloud agent and the back-office network provides connection through VPN tunneling. In some examples, one or more of the imaging devices 112-118 are connected to the cloud via a gateway. The gateway runs the cloud agent and facilitates communication between the imaging device and the cloud.

Imaging devices 112-118 can be registered with the imaging protocol manger 120. Each imaging device can maintain a protocol database which stores protocols used by the device for various scenarios and tasks. After registration, protocols can be imported (i.e., pulled) from the imaging devices 112-118 and stored in the database 124 in the cloud. One or more protocol team(s) (e.g., radiologist, physician, technician, researcher) can access the imaging protocol manager 120 from a user device 130, which can be, for example, a workstation, computer, laptop, or other processing device. In some embodiments, the imaging protocol manger 120 supports a web-based portal or web-based application for the protocol team(s) to access from the user device 130. In further embodiments, a browser-based interface can serve as a zero footprint, zero download, and/or other universal viewer for the user device 130. The protocol team(s) can view, edit, and evaluate the protocols through the web-based portal or application. The user interface of the web-based portal/application may be configured to help or guide a user in accessing data and/or functions to facilitate protocol management. In some embodiments, the user interface may be configured according to certain rules, preferences, and/or functions. Furthermore, a user can customize the interface according to his/her desires, preferences, and/or requirements.

The protocol team(s) can mark certain protocols as "standard" and publish the standard protocols in the protocol library of the database 124 in the cloud. The imaging protocol manager 120 can compare protocols pulled from the imaging devices 112-118 to the standard protocols published in the protocol library 124 and track any deviations. The protocol manager 120 can also distribute (e.g., push) the published protocols to applicable imaging devices.

Figure 2:
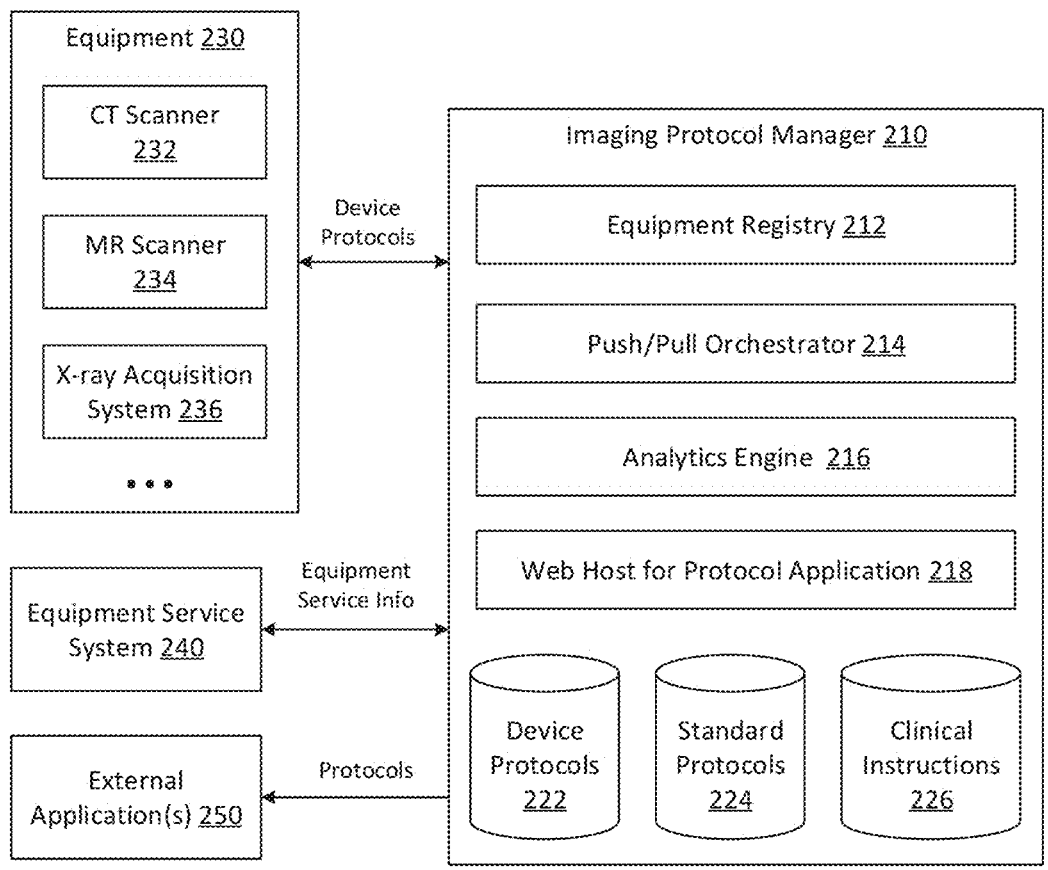
FIG. 2 is a block diagram of an imaging protocol manager in operation, in accordance with an exemplary embodiment.

Referring to FIG. 2, a block diagram of an imaging protocol manager 210 in operation is shown in accordance with certain examples. It should be understood that the devices/systems shown in FIG. 2 that work in conjunction with the imaging protocol manager 210 are for illustration not for limitation. The imaging protocol manager 210 can operate in conjunction with more, fewer, and/or different devices/systems. The imaging protocol manager 210 corresponds to the imaging protocol manager 120 in FIG. 1, which is a cloud-based software solution that helps maintain and standardize imaging protocols for equipment 230 (including CT scanner 232, MR scanner 234, X-ray acquisition system 236, for example) in a centralized way. An equipment service system 240 (e.g., GE Insite™, etc.), which facilitates services to equipment 230, can exchange equipment service information with the imaging protocol manager 210. One or more external application(s) 250 can leverage protocol information from the imaging protocol manager 210. For example, the external application(s) 250 may include an analytics application (e.g., GE DoseWatch™, etc.) that analyzes various parameters indicated in protocols.

As shown in FIG. 2, in some examples, the imaging protocol manager 210 includes an equipment registry 212, push/pull orchestrator 214, analytics engine 216, web host for protocol application 218, and various database including a device protocols database 222, standard protocols database 224, and clinical instructions database 226. Version history of protocols can be maintained, events and activities for a protocol can be logged in the databases.

In operation, the equipment registry 212 registers imaging devices (e.g., CT scanner 232, MR scanner 234, X-ray acquisition system 236) with the protocol manager 210. The push/pull orchestrator 214 coordinates pulling protocols from registered devices to the device protocols database 222. In some examples, clinical instructions are also pulled from the imaging devices and stored in the clinical instructions database 226. The web host for protocol application 218 supports, for example, a web-based portal/application for the protocol team(s) to access the imaging protocol manager 210 from a user device (e.g., user device 130 of FIG. 2). The protocol team(s) can view and edit the protocols stored in the device protocol database 222, and mark some protocols as "standard." The standard protocols are published in the standard protocols database (i.e., library) 224. The push/pull orchestrator 214 further coordinates pushing the published protocols from the standard protocols database 224 to applicable imaging devices.

The analytics engine 216 can perform analysis regarding protocol compliance, equipment operation, protocol changes, and so on. For example, the analytics engine 216 can analyze deviations of protocols (e.g., device protocol versus device protocol, device protocol versus standard protocol, standard protocol versus standard protocol, etc.), and track revisions and changes of protocols. In some examples, the analytics engine 216 can further perform protocol utilization analysis, performance analysis, benchmarking, joint commission compliance analysis, customized analytics for one or more key performance indicators (KPIs), and so on. A radiology administrator of a hospital can leverage the analytics engine 216 to manage compliance and periodic reporting of protocol usage in a clinical practice, for example.

Figure 3:
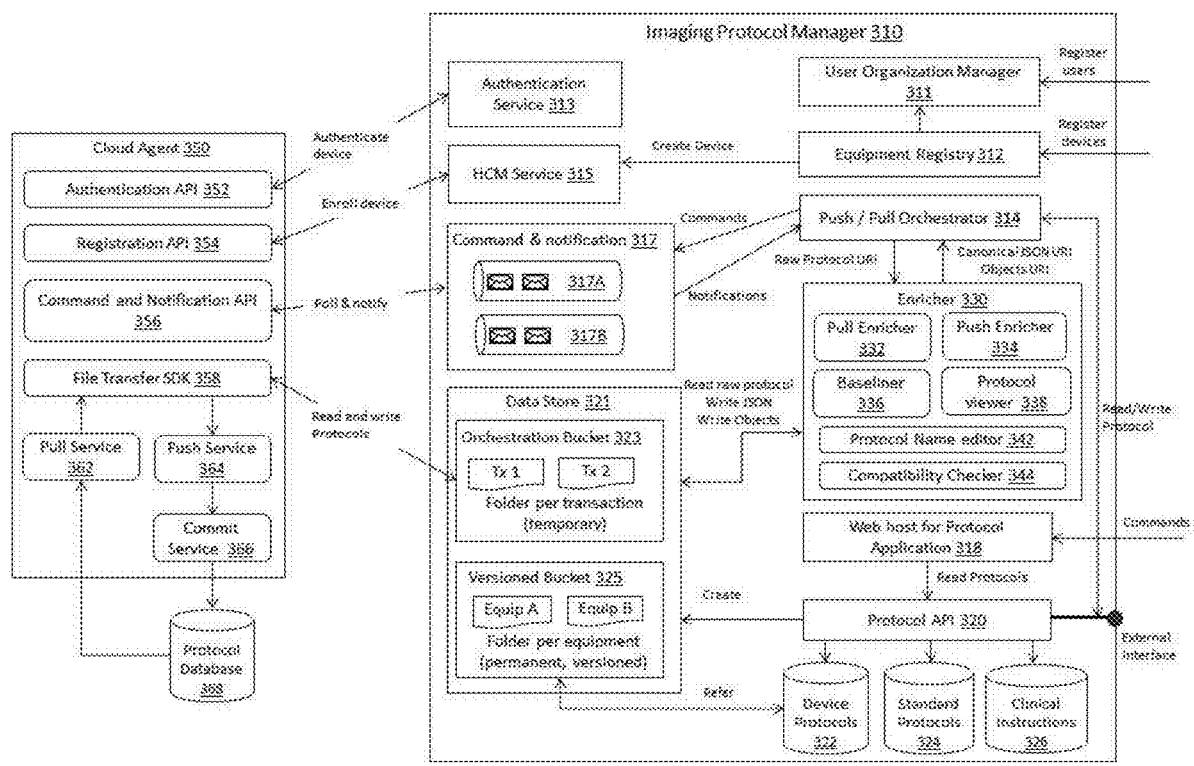
FIG. 3 is a block diagram of an imaging protocol manager in communication with a cloud agent, in accordance with an exemplary embodiment.

Referring to FIG. 3, a block diagram of an imaging protocol manager 310 in operation is shown in accordance with certain examples. The imaging protocol manager 310 corresponds to the imaging protocol manager 120 of FIG. 1, implemented as a cloud-based software application. The cloud-based imaging protocol manager 310 works in conjunction with a cloud agent 350, which may include a client-side software application that talks to the protocol manager 310 securely. In some examples, the client agent 350 runs on an imaging device (e.g., an X-ray machine, CT scanner, MR machine, ultrasound imager, etc.). In some examples, the client agent 350 runs on a back-office network (e.g., an edge services platform, an IoT platform) that facilitates communication between the imaging device and the cloud. In some examples, the client agent 350 runs on a gateway and/or other edge device that facilitates communication between the imaging device and the cloud. In some examples, some components of the client agent 350 run on an imaging device while other components run on the back-office network or the gateway, etc.

As shown in the example of FIG. 3, users can be registered via a user organization manager 311, and equipment can be registered via an equipment registry 312. Thus, imaging devices and users can be added to the imaging protocol manager 310 and stored, alone and/or as part of a hierarchy or organization structure of organization, sites, and devices stored in the user organization manager 311 and/or equipment registry 312. Imaging devices can be associated with device identifiers in the equipment registry 312, which is also used with information such as device name, device model, a device location, device modality (e.g., MR, CT, X-ray), and device status (e.g., ready, activated, connected, disconnected, etc.) to create a device profile or model to be managed by healthcare management services (HCM) module 315. An authentication service module 313 facilitates user and/or device authentication to interact with the imaging protocol manager 310.

In certain examples, the cloud agent 350 uses an authentication application programming interface (API) 352 to authenticate a user and/or imaging device with the authentication services module 313 of the imaging protocol manager 310. A registration API 354 can facilitate enrollment of the imaging device with the HCM services module 315 of the protocol manager 310. Device credentials can be stored by the cloud agent 350 and the equipment registry 312 to facilitate future authentication and connection.

The cloud agent 350, via a command and notification API 356, can interact with the imaging protocol manager 310 via polling and/or notification of a command & notifications module 317. In certain examples, the command & notifications module 317 includes one or more command queues 317A to store commands to be executed by the cloud agent 350 and one or more notification queues 317B to store notifications received from the cloud agent 350.

The push/pull orchestrator 314 regulates pulling of imaging protocol information from a connected imaging device as well as pushing imaging protocol to a connected imaging device. The push/pull orchestrator 314 can generate commands that are stored in the command queue 317A and receive notifications from the notification queue 317B. Additionally, the push/pull orchestrator 314 can provide microservices/lambda functions that orchestrate the pull/push workflow with various microservices/lambda functions, such as concurrency management, job status management, duplication detection, and versioned objects management.

A file transfer software development kit (SDK) 358 at the cloud agent 350 facilitates uploading and downloading of imaging protocols to and from the cloud. Protocol information can be provided to a data store 321 (e.g., a Blob storage, other data storage, etc.) from the file transfer SDK 358 and stored in an orchestration bucket 323 in the data store 321.

The orchestration bucket 323 temporarily stores protocol transactions to be processed. For every pull/push command, a unique transaction identifier (ID) is generated and associated with one or more protocol(s). The protocols uploaded from the device to the imaging protocol manager 310 (or protocols to be pushed to the device from the imaging protocol manager 310) are stored in a transaction folder in the orchestration bucket 323, for example, that is unique per transaction. The data store 321 also includes a versioned bucket 325 which stores various versions of protocols per each piece of equipment (e.g., each imaging device). For example, in the version bucket 325, each piece of equipment has protocol information stored separately by version.

An enricher 330 (e.g., similar to the analytics engine 216 of the example of FIG. 2) processes protocol data. The orchestrator 314 provides raw protocol uniform resource identifiers (URIs) to the enricher 330. The enricher 330 can be modality-specific, for example. The enricher 330 includes a pull enricher 332 for calling appropriate modality-specific functions to convert raw protocols pulled from devices to a uniform format (e.g., JavaScript Object Notation (JSON) format) to be stored in the imaging protocol manager 310. Since protocols from different devices and scanner models can be in different formats, the data stored in the cloud is converted to one single JSON format (e.g., via a pull enricher 332), for example. The enricher 330 also includes a push enricher 334 to process ongoing protocol information to be distributed to the imaging device, which calls modality-specific functions to convert JSON format to raw protocols.

The enricher 330 includes a baseliner 336 that can perform an initial baselining of protocols pulled from a connected imaging device. The process of baselining will be discussed in detail below with reference to FIG. 17. The enricher 330 further includes a protocol viewer 338 for viewing protocol information, a protocol name editor 342 to allow the imaging protocol manager 310 to edit the protocol name in accordance with guidelines, norms, and/or other rules and/or preferences for storage in the protocol libraries 322, 324, etc. A compatibility checker 344 can check compatibility of an incoming protocol with other library protocols, for example. In some examples, the compatibility checker 344 can determine whether an outgoing protocol is compatible with the target imaging device. Using the baseliner 336, the protocol viewer 336, the compatibility checker 344, etc., the enricher 330 can process imaging protocol information pulled from the imaging device and manage imaging device adherence to protocol(s) by comparing device protocol(s) to library protocol(s).

The imaging protocol manager 310 can receive one or more commands (e.g., from a user, from an imaging system, from a healthcare information system, from a radiology reading workstation, etc.) through the web host for protocol application 318, which enables a web-based portal/application for users to access the imaging protocol manger 310 using a processing device. The commands may include, for example, listing available protocol(s) (e.g., of a certain type, for a certain device, etc.), searching for a particular protocol/protocol type, tagging protocol(s) (e.g., with a device type, hospital association, patient type association, condition association, etc.), publishing protocol(s) (e.g., to a standards body, to participating customers/members, to a shared database, etc.), pushing protocols, and so on. In certain examples, the web host 318 supports user interface components that allow users to manage protocols by creating library structures, import protocols into the library(-ies) 322, 324, baseline a device in conjunction with the baseliner 336, search and compare protocols, etc.

The web host 318 leverages a protocol API 320. The protocol API 320 represents a defined format used by a front-end application to interact with the databases (e.g., databases 322-326). The protocol API 320 can be used by the web host 318 to execute commands with respect to the device protocols database 322, the standard protocols database 324, the clinical instructions database 326, etc. The protocol API 320 can be used to list protocols, search and compare protocols, browse, view and edit protocols, push protocols, etc. In some embodiments, external applications (e.g., external application(s) 250) uses the protocol API 320 as an interface to leverage protocol information stored in the device protocols database 322, the standard protocols database 324, the clinical instructions database 326.

In certain examples, a user can view connected device(s) and browse protocols 322, 324 and associated clinical instructions 326 via the protocol API 320. In certain examples, protocols can be compared, and technical settings associated with a protocol (e.g., a master protocol, etc.) can be viewed.

In certain examples, a selected protocol can be marked as a "standard" protocol within an organization. A standard protocol or set of standard protocols for a particular scanner model can be published (e.g., within an organization, to another approved organization, etc.) and accessed via the protocol API 320 (e.g., available via the versioned bucket 325 of the data stores 321 and/or via the external interface, etc.). In certain examples, a device protocol 322 can be viewed in a scanner folder 325, and/or a standard protocol in database 324 can be viewed in a standard library, etc.

In some examples, the device protocols database 322, the standard protocols database 324, the clinical instructions database 326 are implemented as separate databases. In other examples, the device protocols 322, standard protocols 324, and clinical instructions 326 are implemented as parts or sections of the same database. The protocol API 320 can also be called by the push/pull orchestrator 314 to read/write protocols from/to the databases.

Protocols can be distributed by pushing standard protocols from the standard protocols database 324 to applicable scanner model(s) within an organization, for example. A status of pull and distribution can be displayed and/or modified, for example. In certain examples, protocols stored in the databases 322-326 can be edited, renamed, etc. One or more logs and/or reports can be maintained to track what protocols are pushed/pulled, who is pushing/pulling the protocols, what protocols are edited, etc.

At the cloud agent 350, a pull service module 362 pulls protocol information from a protocol database 368 associated with the imaging device to be provided by the file transfer SDK 358 to the data store 321 of the imaging protocol manager 310. A push service module 364 receives protocol information from the imaging protocol manager 310 downloaded by the file transfer SDK 358 and formats and provides the protocol information (e.g., including technical instructions and clinical instructions) to a commit service module 366, which commits the protocol information into the protocol database 368 for use by one or more associated imaging devices.

Thus, the imaging protocol manager 310, used in conjunction with the cloud agent 350, can manage uploading, editing, downloading, and monitoring of protocols for multiple modalities and device types across an organization. The cloud-based protocol solution can manage planned/scheduled protocol prescription for scanners such as CT, MR, x-ray, etc., imaging systems. In certain examples, device protocol data is pulled from an imaging device via a healthcare gateway (e.g., the cloud agent 350, etc.) and transferred to a virtual private cloud housing the imaging protocol manager 310 where the protocol data can be summarized and presented to customers via a web application. In certain examples, while cloud infrastructure (e.g., GE Health Cloud with Predix™, etc.) is leveraged, the imaging protocol manager 310 can be provided as a stand-alone application.

In certain examples, the imaging protocol manager 310 allows users to monitor device protocol configuration at an enterprise level. Using the imaging protocol manager 310, a user can manage device-specific database 322 and/or standard protocol library(-ies) 324 in the cloud and support protocol standardization across multiple facilities. The imaging protocol manager 310 can help identify protocol variation and provide actionable insight. The imaging protocol manager 310 can also help users manage compliance with requirements from regulatory bodies, accrediting organizations, etc.

Figure 4A:
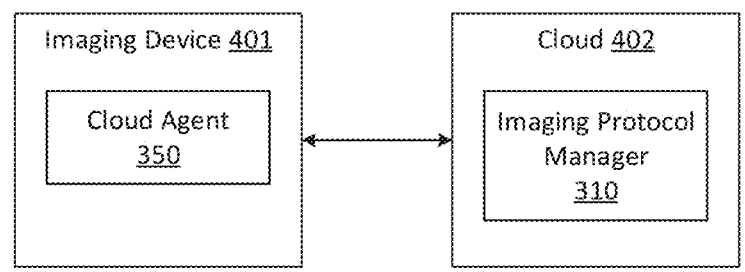
FIGS. 4A-4B illustrate cloud agent configurations with respect to the imaging protocol manager of the example of FIG. 3, in accordance with exemplary embodiments.
Figure 4B:
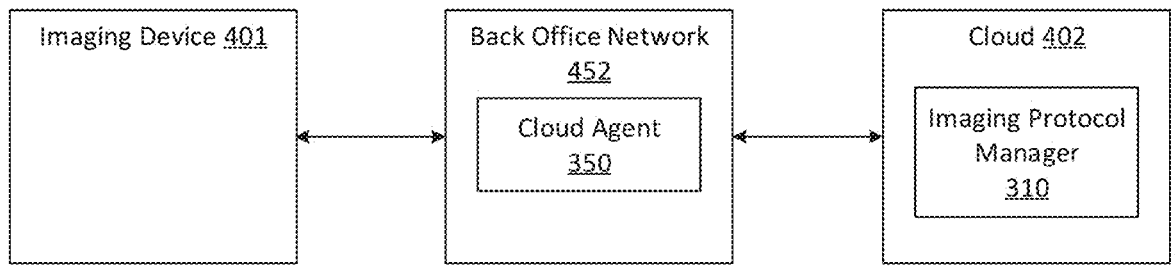

In certain examples, the cloud agent 350 is integrated with the imaging device 401 (e.g., CT scanner 232, MR scanner 234, X-ray acquisition system 236) and facilitates point-to-point communication between the respective device and the imaging protocol manager 210, 310. In other examples, the cloud agent 350 is implemented in a back-office network, which serves as an intermediary between the imaging device 401 and the imaging protocol manager 210, 310. FIG. 4A shows an example configuration 400 in which the cloud agent 350 is integrated with the imaging device 401 and facilitates point-to-point communication between the imaging device 401 and the imaging protocol manager 310 residing in a cloud 402. In another example configuration 450, shown in FIG. 4B, the cloud agent 350 is implemented in a back-office network 452, which serves as an intermediary between the imaging device 401 and the cloud 402 with the imaging protocol manager 310.

Figure 5:
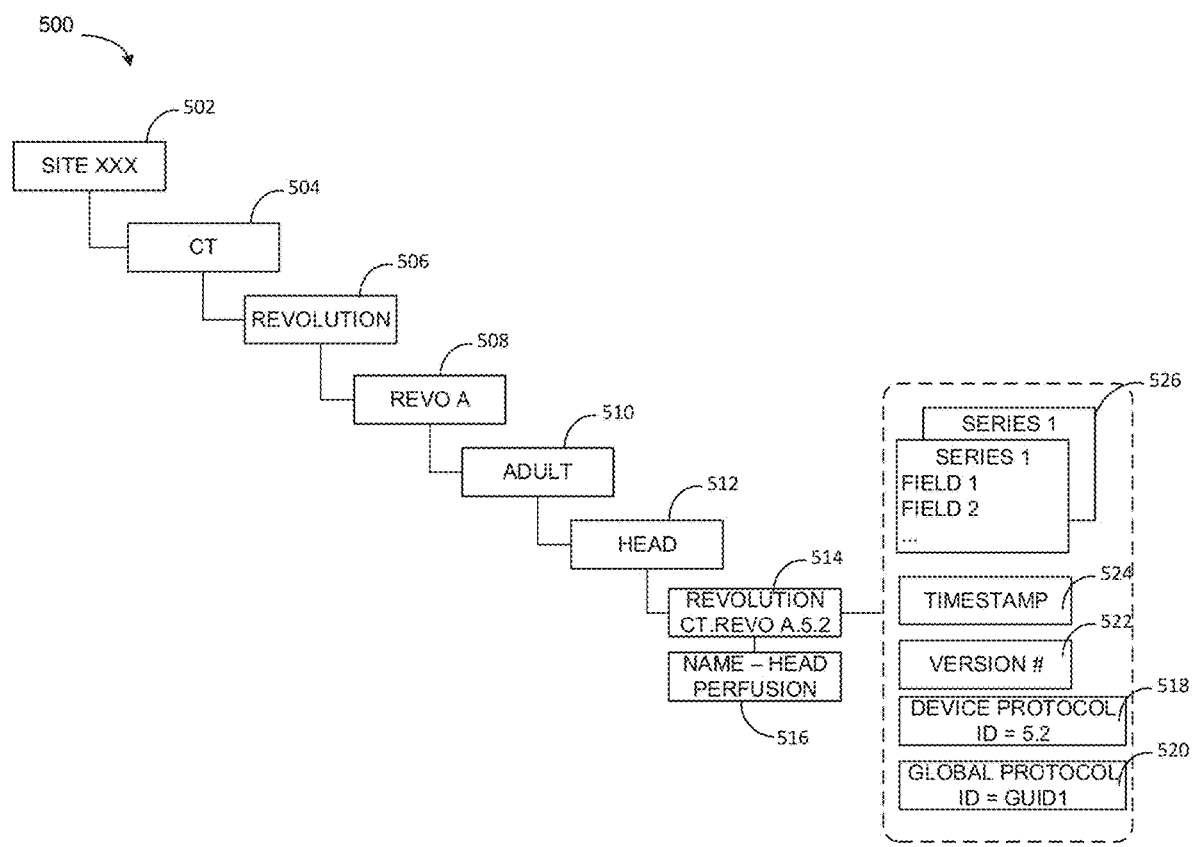
FIGS. 5-6 illustrate protocol definitions, in accordance with exemplary embodiments.
Figure 6:
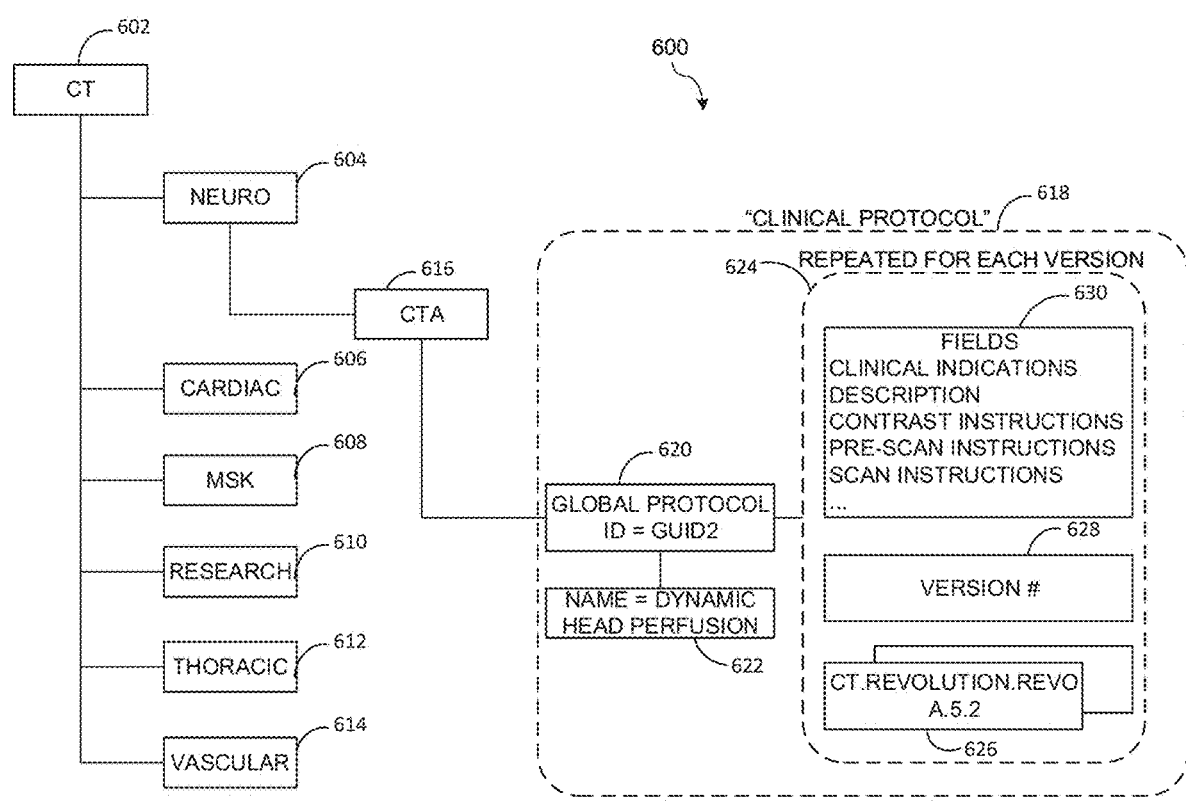

FIGS. 5-6 illustrate logical views 500, 600 of example imaging protocols, organized in a hierarchy of device type, specific device, purpose/reason for exam, and particular target information. Device protocols are identified by the imaging protocol manager 310, cloud agent 350, and imaging device based on a unique protocol ID (e.g., GUID, etc.). Available versions of available device protocols can be tracked. When a device protocol is first pulled into the device protocols database 322 (or standard library 324), it is assigned a globally unique ID (GUID) and tagged as Version 1, for example. On subsequent pulls, if the protocol's content changes on the device, a new object is added with an incremented version number.

As shown in the example of FIG. 5, the example imaging protocol view 500 specifies a location 502 (e.g., a hospital and/or other healthcare site, etc.), an imaging modality 504 (e.g., CT, MR, X-ray, NM, etc.), a device type 506 (e.g., GE Revolution™ etc.), a device model 508 (e.g., GE Revo ATM, etc.), a patient type 510 (e.g., adult, teen, child, infant, etc.), a body part 512 (e.g., head, chest, limb, torso, body, cardiac, respiratory, etc.), a protocol identifier 514 (e.g., Revolution CT.Revo A.5.2, etc.), and a protocol name 516 (e.g., "Head Perfusion", "Routine Head", "Helical Head", "Soft Tissue Neck", "Circle of Willis", "Lower Extremity", "Routine Chest", "Pulmonary Embolis", "Lung Assessment", "Abdomen Pelvis", "Aorta Runoff", "Aortic Dissection", "CT Colonography", "Dual Liver", "L-spine Survey", "Cardia Angio", etc.).

The protocol identifier 514 allows a definition (e.g., technical settings and/or other instructions, etc.) of the imaging protocol to be retrieved. As shown in the example of FIG. 5, the protocol can be associated with a device protocol ID 518 and a global protocol ID 520. The protocol definition also includes a version number 522 and a timestamp 524 at which the protocol definition was obtained. Thus, multiple versions of a protocol can be tracked and organized according to timestamp 542 and version 522. The protocol definition also includes a parameterization of image series 526 and associated fields for image data acquisition and/or display according to the protocol.

Via the imaging protocol manager 310, clinical protocols can be created and edited in the cloud 402. Clinical protocols can be organized in hierarchies. The hierarchy structure can be automatically determined and/or configured based on user input. Clinical protocols are associated with one or more device protocols. In certain examples, a clinical protocol library resides in the cloud. Clinical protocols include clinical instructions and associated device protocols. In certain examples, clinical protocols are associated with one or more versions. For example, when a clinical protocol is first created, the protocol is assigned Version 1. Each time the user edits the clinical protocol or modifies its device protocol associations, a new object is added with an incremented version number. In certain examples, the version of the clinical protocol is not updated when the version number of an associated device protocol changes. Rather, the version number is updated when the association with device protocols changes.

FIG. 6 illustrates an example imaging protocol hierarchy 600 including a plurality of protocols for a particular imaging modality 602. For the modality 602, a plurality of imaging protocol types 604-614 (e.g., neuro, cardiac, musculoskeletal (MSK), research, thoracic, vascular, etc.) can be defined for the modality 602 (e.g., CT, MR, NM, X-ray, ultrasound, etc.). For a particular type 604-614, an imaging protocol 616 is defined. As shown in the example of FIG. 6, a clinical protocol definition 618 is provided including a global protocol ID 620 and a protocol name 622 associated with the protocol definition 618. In certain examples, such as shown in FIG. 6, the protocol definition 618 can include a plurality of versions, and each version includes a protocol version definition 624. The version definition 624 includes a protocol version identifier 626, a version number 628, and a definition of protocol fields 630.

Figure 7:
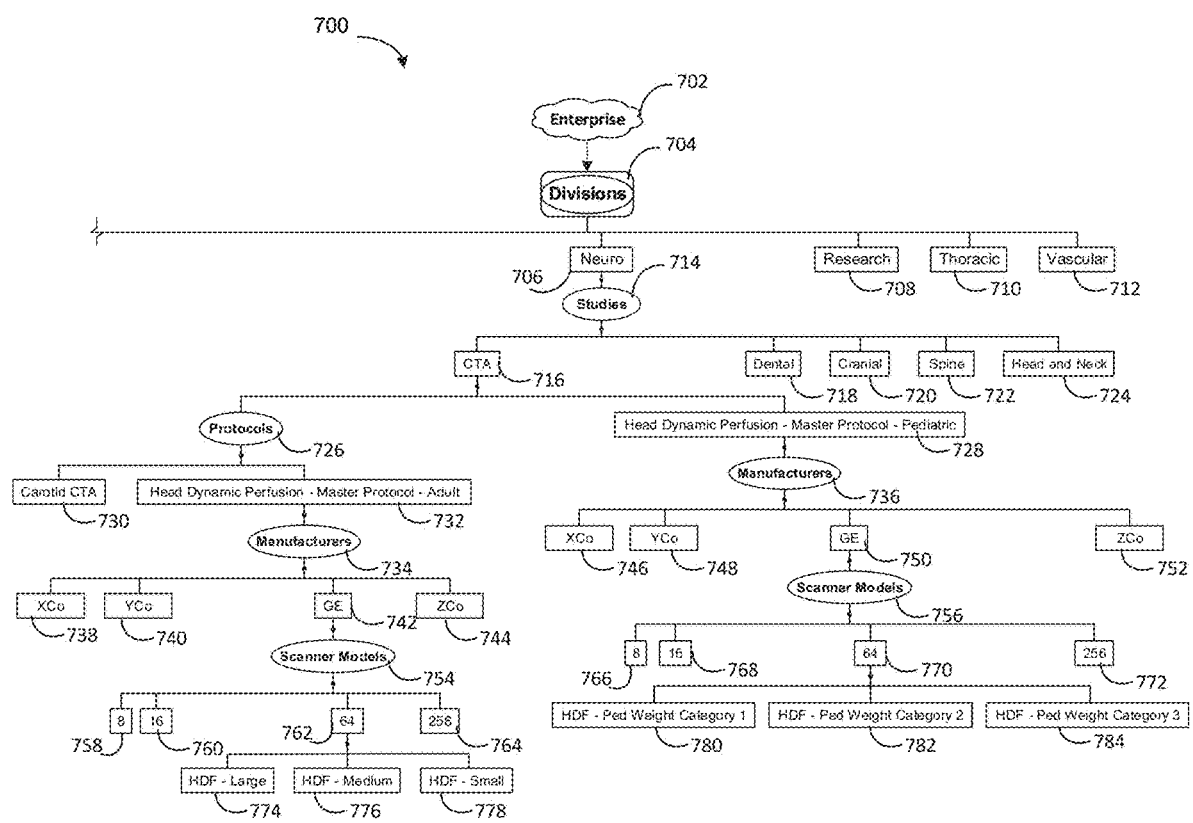
FIG. 7 illustrates a hierarchy of imaging protocols for a particular enterprise, in accordance with an exemplary embodiment.

As described above, imaging protocols can be organized according to type, modality, organization, and/or other hierarchy, for example. FIG. 7 illustrates an example hierarchy 700 of imaging protocols for a particular enterprise 702. The example enterprise 702 is divided and/or otherwise organized according to divisions 704 including neuro 706, research 708, thoracic 710, vascular 712, etc. Each division 706-712 includes one or more study types 714 including computed tomography angiography (CTA) 716, dental 718, cranial 720, spinal 722, head and neck 724, etc. For each study type 714, one or more imaging protocols 726, 728 are specified. For example, as shown in FIG. 7, a single protocol 728 (e.g., a master protocol for a pediatric head dynamic perfusion, etc.) can be provided. A plurality of protocols 730, 732 can also be provided in a subset 726.

For a given protocol 728, 732, protocol information can be organized according to manufacturer 734, 736. Each imaging device manufacturer 738-752 has associated scanner models 754, 756. For each scanner model 758-772, size and/or target type constraints 774-784 can further subdivide the imaging protocol definition, organization, and storage.

Figure 8:
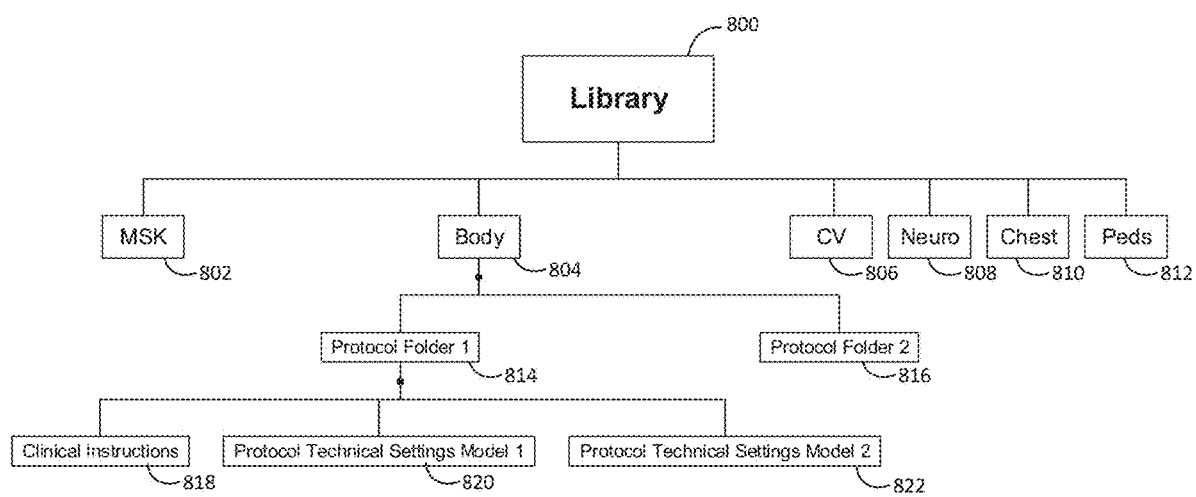
FIG. 8 depicts a protocol library storing and organizing imaging protocols according to one or more criterion, in accordance with an exemplary embodiment.

FIG. 8 depicts an example protocol library 800 storing and organizing imaging protocols according to one or more criterion. The example library 800 includes a plurality of protocol types such as MSK 802, body 804, cardiovascular (CV) 806, neuro 808, chest 810, pediatric 812, etc. For a particular protocol type 802-812, available imaging protocols can be divided among a plurality of protocol folders 814, 816. In each protocol folder 814, 816, protocol definition information is saved. For example, clinical instructions 818 forming part of the imaging protocol describe how to perform an imaging scan (e.g., including patient positioning, contrast procedure, etc.). Technical settings 820, 822 provide parameters and/or other configuration information for the imaging device. As shown in the example of FIG. 8, multiple technical settings models 820, 822 can be provided for selection in conjunction with the clinical instructions 818. Appropriate technical settings 820, 822 can be selected for use with the clinical instructions 818 to configure the imaging device for image acquisition and analysis.

Figure 9:
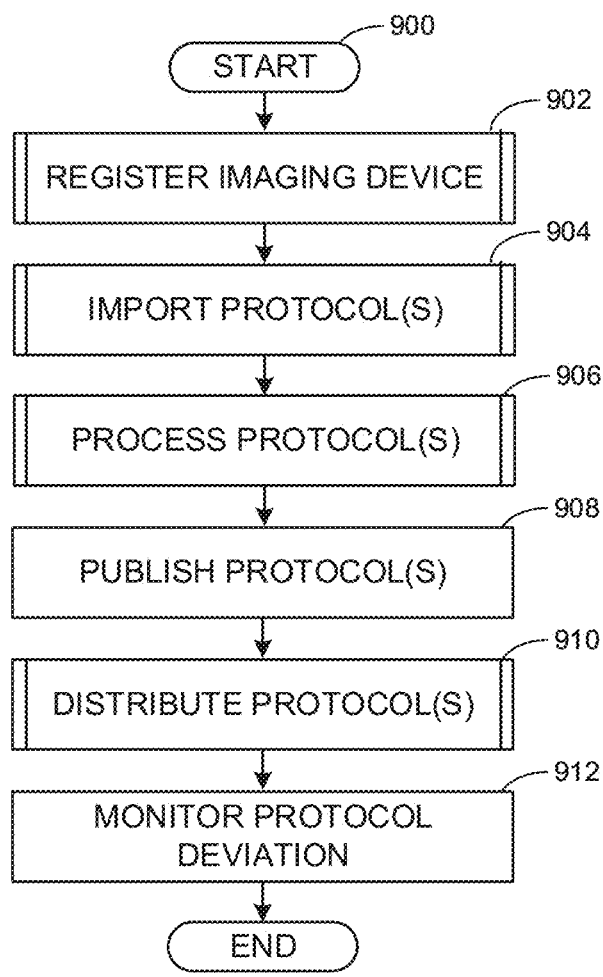
FIG. 9 illustrates a flow diagram of an example imaging protocol management process, in accordance with an exemplary embodiment.

The imaging protocol manager 310, in conjunction with the cloud agent 350, facilitates a protocol management workflow such as the workflow 900 illustrated in the example of FIG. 9. The imaging protocol manager 310 and the cloud agent 350 execute a protocol management workflow (see, e.g., FIG. 9) including the following processes: (1) registering imaging devices with the protocol manager (see, e.g., FIG. 12); (2) pulling protocols and, in some examples, clinical instructions, from imaging devices to the protocol manager (see, e.g., FIG. 14); (3) analyzing protocol deviations (see, e.g., FIG. 16); and (4) pushing standard protocols from the protocol manager to applicable imaging devices (see, e.g., FIG. 21).

FIG. 9 illustrates a flow diagram of an example imaging protocol management process 900. At operation 902, an imaging device 232-236 is registered with the equipment registry 312 associated with the imaging protocol manager 310. For example, the cloud agent 350 (located on the respective imaging device 232-236 and/or the back-office network 452, etc.) communicates with the imaging protocol manager 310 to identify the device 232-236 including authentication between the authentication API 352 and the authentication service 313 and registration between the registration API 354, HCM services 315, and the equipment registry 312.

At operation 904, imaging protocol(s) are imported (e.g., "pulled") from the imaging device 232-236 into the device protocol library 322 and/or the standard protocol library 324 (which can be collectively implemented as the "protocol library", etc.) of the imaging protocol manager 310. For example, the pull orchestrator 314 triggers a command to the cloud agent 350 to activate the pull service 362 to retrieve protocol information from the device 232-236 (e.g., directly and/or via the back-office network 452, etc.) and push the information to the imaging protocol manager 310. At the imaging protocol manager 310, the protocol information is stored for further processing. Pulled protocol information can include technical settings and/or clinical instructions, for example.

At operation 906, the imported protocol(s) are processed by the imaging protocol manager 310. For example, the protocol(s) from the imaging device 232-236 can be baselined by the baseliner 336 to determine a current/base configuration of the device 232-236, which can be used for comparison to evaluate differences between devices, differences between protocols, changes in device protocol since last import, etc. Using the baseliner 336 determination, new protocol(s) can be identified from the device 232-236 and deviation from library protocol(s) 322, 324 can be identified and a resolution determined such as 1) to replace the deviating device protocol with a protocol from the device library 322 or the standard library 324; 2) create a new device protocol for the device 232-236 (e.g., new device imaging protocol, new device imaging protocol version, etc.) to be stored in the device protocol library 322; 3) replace an old device protocol in the device protocol library 322; 4) create a new standard protocol to be stored in the standard protocol library 322; 5) replace an old standard protocol in the standard protocol library; etc.

Figure 10:
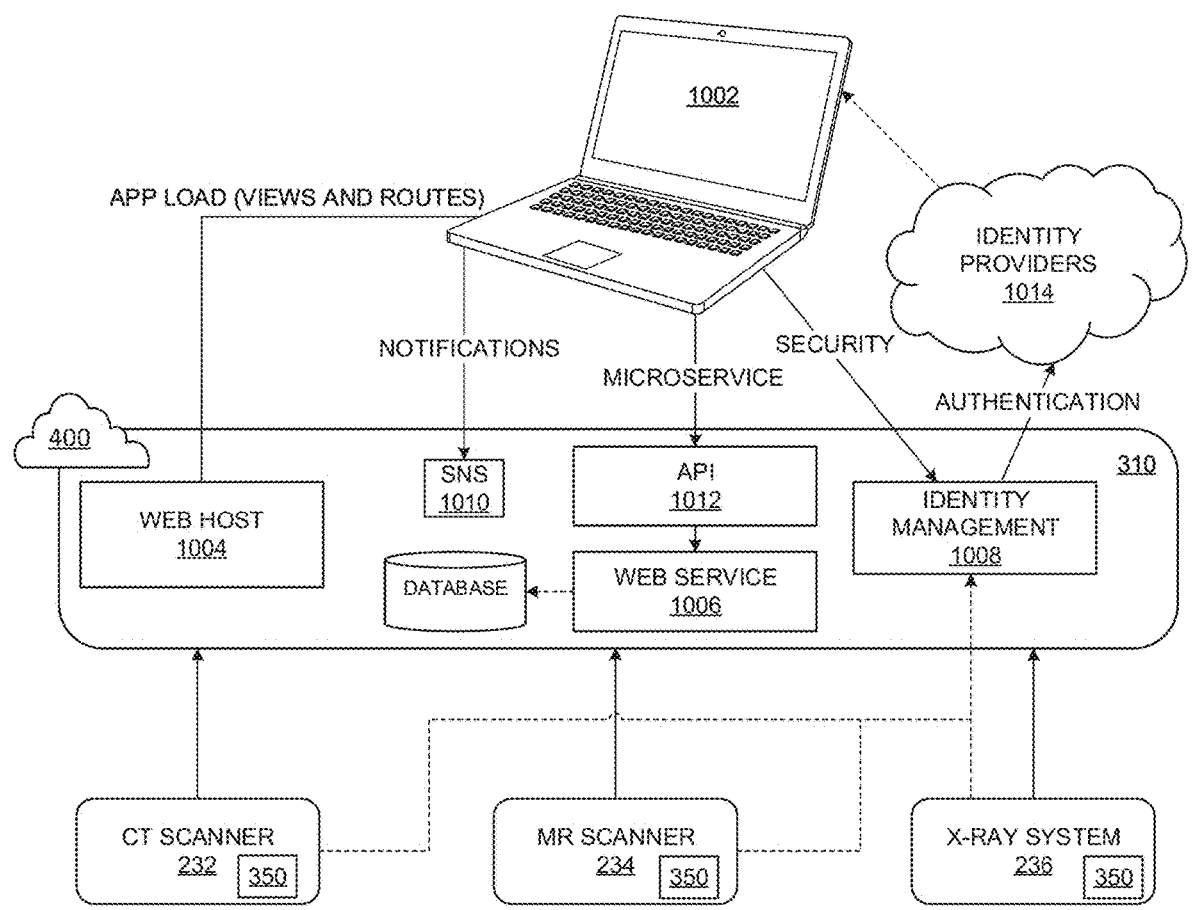
FIG. 10 illustrates an example system by which a computing device with a browser can access the imaging protocol manager of FIG. 3, in accordance with an exemplary embodiment.

At operation 908, protocol(s) are published as standard protocols for an organization or other enterprise of devices 232-236. For example, the protocol(s) pulled from the device 232-236 that the protocol manager 310 has determined should apply to multiple devices 232-236 of the same type can be published via the standard protocol library 324. The library(-ies) 322, 324, as well as associated clinical instructions 326, can be accessed via a browser and/or protocol management application running on a computing device such as a workstation, laptop, tablet computer, smart phone, and/or other computing device. FIG. 10 illustrates an example system 1000 by which a workstation 1010 with a browser can access the imaging protocol manager 310.

FIG. 10 illustrates an example deployment of the imaging protocol manager 402 with respect to devices 232-236 and a workstation 1002 with browser and/or other application for imaging protocol management. Via the cloud 400, the imaging protocol manager 310 leverages a web host 1004, web services 1006, identity management 1008, a simple notification service (SNS) 1010, and APIs 1012 to communicate protocol, status, application, and/or other information between the workstation 1002 and devices 232-236. The workstation 1002 provides notifications to the SNS 1010, microservices to the API 1012, security information to the identity management 1008, and receives authentication of identity via one or more identity providers 1014 and application loading for protocol management, etc.

At operation 910, protocols are distributed to device(s) 232-236 within the organization. For example, device(s) 232-236 having protocol(s) out of compliance with organizational requirements, clinical guidelines, latest version, and/or other best practice are identified by the imaging protocol manager 310 based on status information from the cloud agent 350 and/or other equipment registration information provided. Such a push of protocol information from the protocol manager 310 to device(s) 232-236 can be triggered via the workstation 1002 of the example of FIG. 10, for example.

At operation 912, protocol deviation is monitored and evaluated between a device 232-236 and the corresponding standard protocol 324 on the cloud. Depending upon rules, preferences, and/or other configuration, a device protocol 322 can be maintained for a particular device 232-236 and/or type of device, and/or the device's protocol can be replaced with a corresponding standard protocol 324 to bring the device 232-236 in compliance with the standard. Devices, protocols, etc., can be compared to generate reports, reminders, alerts, next actions, etc.

Figure 11:
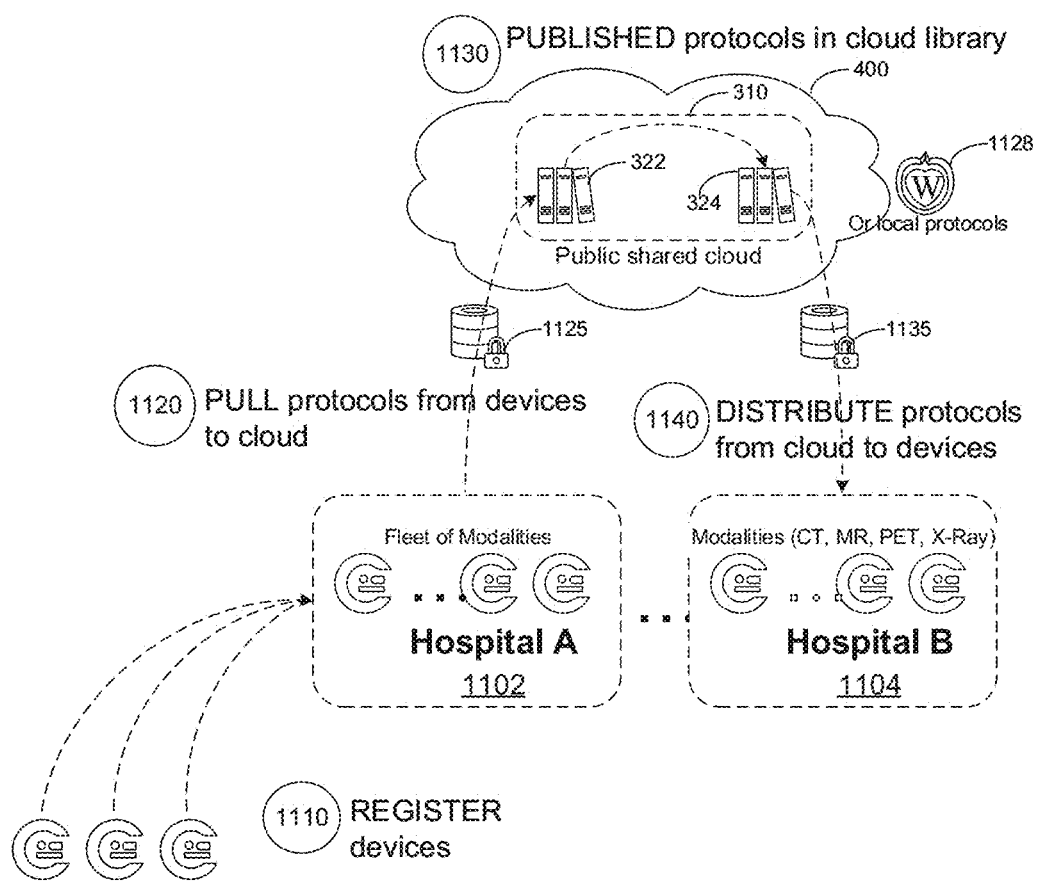
FIG. 11 illustrates an example implementation of a system including the imaging protocol manager of FIG. 3 applying the process of FIG. 9 to an organization including multiple hospitals, in accordance with an exemplary embodiment.

Thus, imaging devices 232-236 can be registered and processed to pull their imaging protocol(s), analyze the pulled protocol(s), update protocol information at the imaging protocol manager 310 and/or respective device 232-236, and monitor protocol usage to help ensure accuracy, compliance, safety, and improved patient care. FIG. 11 illustrates an example implementation applying the process 900 to an organization including multiple hospitals 1102, 1104. At block 1110 in the example of FIG. 11, imaging devices are registered at hospital A 1102. At block 1120, imaging protocols are pulled from the imaging devices at hospital A 1102 to the cloud 400 via a first cloud agent 1125. Pulled protocol information can be stored in the cloud 400 at the imaging protocol manager 310 as device protocol 322 and/or standard protocol 324 information (e.g., with associated clinical instructions 326). At block 1130, protocols can be published in the cloud library 324, for example. Protocol information can also be stored as a local protocol 1132 information, for example. At block 1140, protocol(s) can be distributed from the cloud 400 to imaging devices at hospital B 1104 via a second cloud agent 1135. Thus, imaging protocol information learned from hospital A 1102 can be processed by the imaging protocol manager 310 and provided to imaging devices at hospital B 1104 using cloud agents 1125, 1135, for example.

An example process 1200 of registering imaging devices with the protocol manager is illustrated in detail with reference to at least FIGS. 3 and 12. Imaging devices 232-236 within an organization (e.g., hospital, clinic) are to be registered with the protocol manager 310 so that their protocols can be managed by the protocol manager 310.

Figure 12:
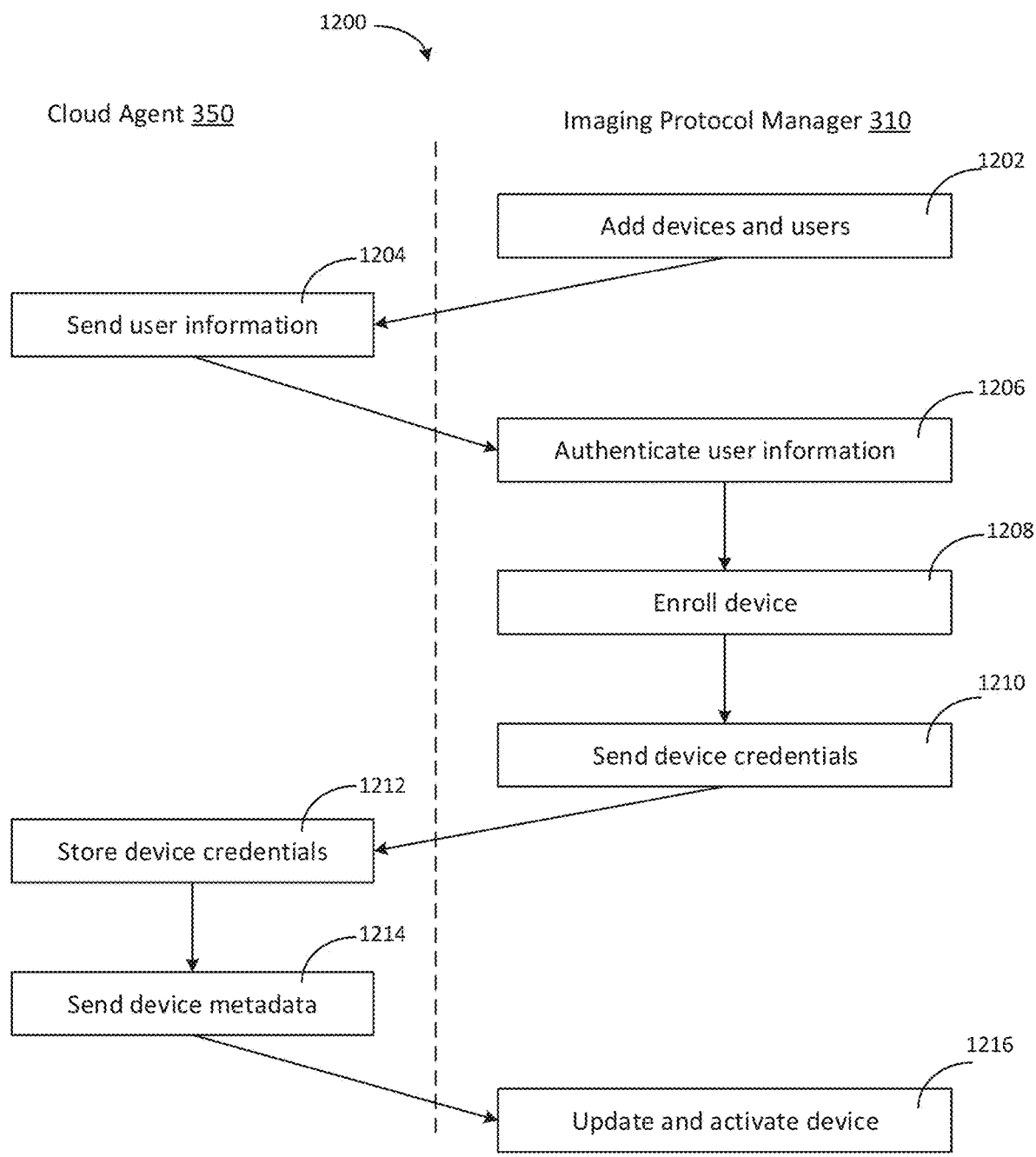
FIG. 12 provides further detail regarding implementation of an operation of the process of FIG. 9 to register device(s) with the imaging protocol manager via the cloud agent of the example of FIG. 3, in accordance with an exemplary embodiment.

FIG. 12 provides further detail regarding an example implementation of operation 902 to register device(s) 232-236 with the imaging protocol manager 310 via the cloud agent 350. A dashed line is used in FIG. 12 to schematically separate the cloud agent 350 and the imaging protocol 310. At operation 1202, imaging devices and users are added at the imaging protocol manager 310. In some embodiments, an administrator for the protocol manager creates a structure of organization, sites, and devices through the equipment registry 312. The equipment registry 312 creates device profiles managed by the healthcare management (HCM) services module 315. The device profile includes a unique device identifier (ID) given to each device and other device information, such as a device name, model of the device, a name of site where the device is located, a modality name (e.g., MR, CT, X-ray), and a status of the device (e.g., ready, activated, connected, disconnected, etc.) associated with the device ID. The administrator creates user accounts for the organization to grant users (e.g., radiologists, physicists, technologists, researchers, etc.) access to the protocol manager 310. In some embodiments, different users have different roles and/or access permissions. The user organization manager 311 stores the user accounts information, such as user ID, password, profile, permission level, etc.

At operation 1204, user information is sent from the cloud agent 350 to the protocol manager 310 for authentication. For example, the administrator or a user who has permission to enroll an imaging device inputs the user information via a user interface (e.g., a graphical user interface) provided at, for example, the device console. The user information includes, for example, user ID, password, the uniform resource locator (URL) for activation and/or any appropriate information. The registration application programming interface (API) 354 at the cloud agent 350 captures the user information and sends to the healthcare management (HCM) services module 315 at the cloud for authentication.

At operation 1206, the user information is authenticated at the protocol manager 310. The HCM services module 315 compares the received user information with the user account stored in the user organization manager 311. If the user information matches the user account, the user information is authenticated. If the user information does not match the user account, the HCM services 315 may return a message to the cloud agent 350, indicating the failure of authentication.

At an operation 1208, the device is enrolled at the protocol manager 310. The HCM services module 315 creates the profile for the device with a status as "enrolled."

At operation 1210, device credentials are sent from the protocol manager 310 to the cloud agent 350. An imaging device needs to be authenticated from time to time to avail itself of services provided by the protocol manager 310. The device credentials are used for authenticating the device.

At operation 1212, device credentials are received and stored by the cloud agent 350. When the imaging devices needs to be authenticated later on, the authentication API 352 can send the stored device credentials to the authentication service module 313 in the cloud to connect to the cloud securely.

At operation 1214, device metadata is sent from the cloud agent 350 to the protocol manager 310. The device metadata may include modality of the device, manufacturer, model, software version, language preference, and so on.

At operation 1216, device information is updated and the device is activated at the protocol manager 310. The HCM services module 315 updates the device information in the cloud with the received device metadata. The status of the device is changed to "activated," which means that the device is registered and ready for transactions with the protocol manager 310. In some embodiments, a user can view a list of registered devices via the web-based portal/application enabled by the web host 318. In further embodiments, the list of devices can break down by modality, site, model, etc.

It should be understood that the registration process described with reference to FIG. 12 is for purposes of illustration only and not for limitation. Any suitable registration process with more, fewer, and/or different operations can be implemented to register imaging devices with the protocol manager. For example, the administrator may send email invitation to users containing URL for device registration.

Figure 13:
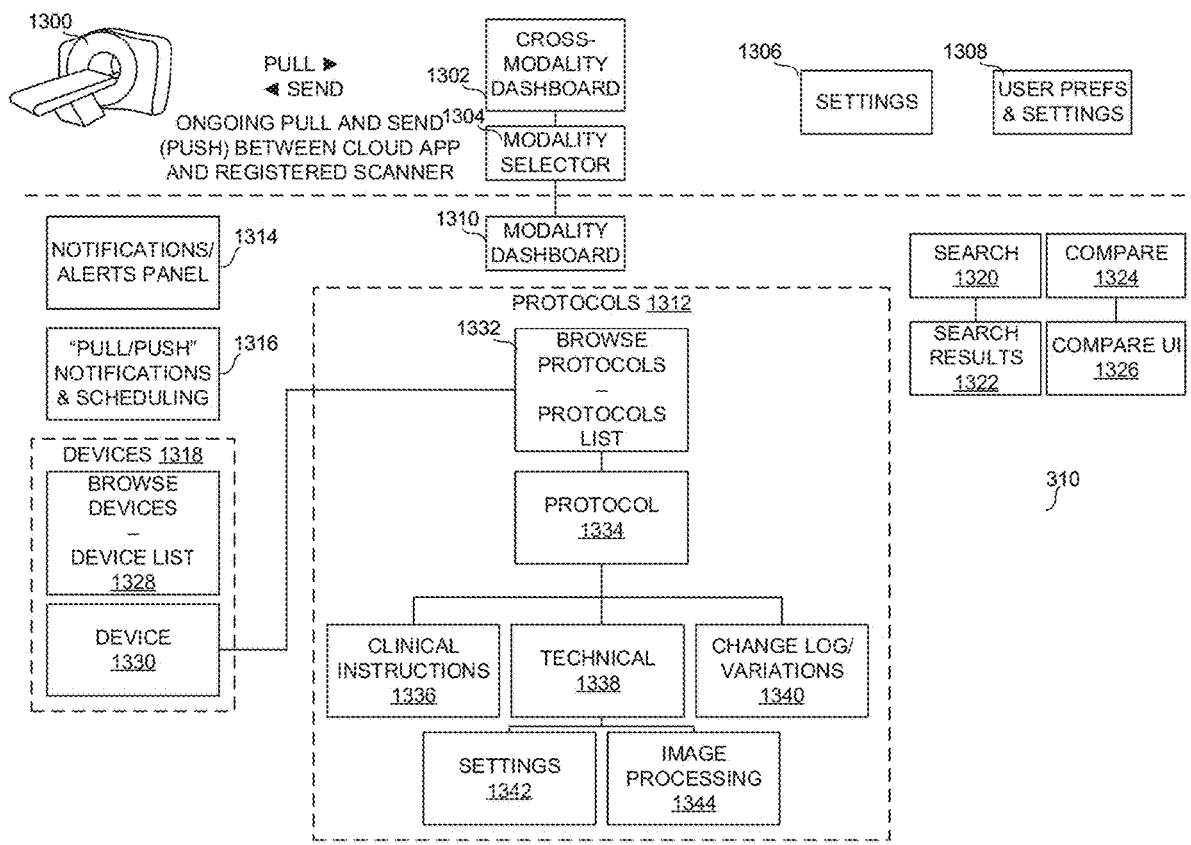
FIG. 13 provides a visualization of an ongoing pull and push protocol interaction between the imaging protocol manager of FIG. 3 and a registered imaging device, in accordance with an exemplary embodiment.

FIG. 13 provides a visualization of an ongoing pull and push protocol interaction between the imaging protocol manager 310 and a registered imaging device 1300 (e.g., one of the imaging devices 232-236, etc.). As shown in the example of FIG. 13, the protocol application provides a cross-modality dashboard 1302 and modality selector 1304 to allow the user to review and select a protocol for a particular modality and view information regarding that protocol on the imaging device 1300, at the imaging protocol manager 310, etc. Additionally, settings 1306, user preferences 1308, etc., allow the user to customize his or her interaction with the device 1300, the protocol manager 310, etc. The user can review available protocols, trigger an upload of protocol information to the imaging protocol manager 130, initiate a download of protocol information to the device 1300, etc.

The cloud image protocol manager 310 provides a corresponding modality dashboard 1310, and protocols 1312, as well as a notifications/alerts panel 1314, pull/push notifications and scheduling 1316, etc., to facilitate exchange of information and functionality, notifications, etc. Further, device information 1318 include a device list 1328 and one or more device models 1330. The protocol information 1312 includes a protocol list 1332 including one or more protocols 1334. For a selected protocol 1334, the protocol 1335 includes clinical instructions 1336 and technical settings 1338, as well as a change log/variation 1340 indicating changes made to the protocol 1334, device variation information, etc. Technical settings 1338 can include device configuration settings 1342, as well as image processing parameters 1344, etc. Further, the imaging protocol manager 310 can facilitate search 1320 for particular protocol standard(s), device protocol(s), etc., and can provide search results 1322 based on a query. Compare 1324 facilitates protocol comparison and display of protocol comparison results to show deviations, compliance, etc., via a comparison user interface 1326.

Example Protocol Intake and Processing Systems and Methods

An example process 1400 of importing protocols from an imaging device to the protocol manager is illustrated in detail with reference to at least FIGS. 3 and 14, according to certain examples. When an imaging device 232-236 has been registered and is connected to the protocol manager 310 for the first time, all protocols from the imaging device 232-236 are automatically uploaded to the imaging protocol manager 310. Afterwards, protocol changes/updates at the imaging device 232-236 are pulled to the imaging protocol manager 310 to update their respective copies in the cloud. The protocol synchronization can happen at a scheduled time (e.g., daily, weekly, etc.). The scheduled time can be configured by a user via the web-based portal/application enabled by the web host 318. In some examples, on-demand synchronization can be performed (e.g., by user selection, event trigger, etc.).

Figure 14:
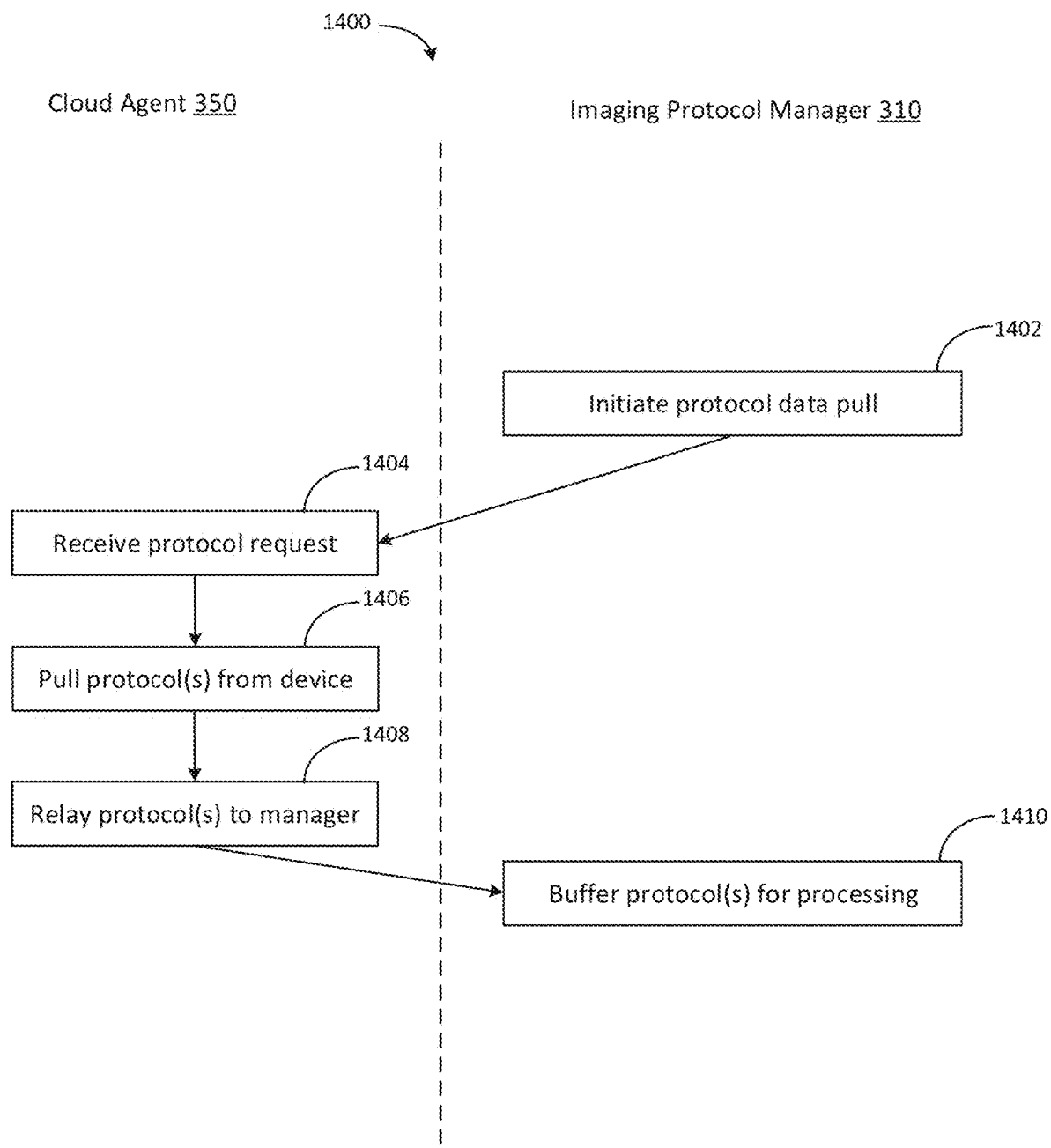
FIG. 14 provides further detail regarding implementation of an operation of the process of FIG. 9 to import protocols from an imaging device with the imaging protocol manager via the cloud agent of the example of FIG. 3, in accordance with an exemplary embodiment.

FIG. 14 provides further detail regarding implementation of operation 904 to import protocols from an imaging device 232-236 with the imaging protocol manager 310 via the cloud agent 350, in accordance with an exemplary embodiment. At operation 1402, the imaging protocol manager 310 initiates a retrieval or "pull" of imaging protocol information from an imaging device 232-236 via the cloud agent 350. For example, the push/pull orchestrator 314 initiates a command to the command and notification module 317 which communicates with the command and notification API 356 of the cloud agent 350 to pull one or more imaging protocols from the imaging device 232-236.

At operation 1404, a protocol request is received at the cloud agent 350 for the imaging device 232-236. For example, the command and notification API 356 at the cloud agent 350 receives the command from the command & notification module 317 at the imaging protocol manager 310 to initiate the pull service module 362 at the cloud agent 350 to pull one or more imaging protocols from the imaging device 232-236 in communication with the cloud agent 350 (e.g., the cloud agent 350 integrated with the imaging device 232-236 and/or communicating with the imaging device 232-236 via the back-office network 452, etc.).

At operation 1406, protocol(s) are retrieved from the imaging device 232-236 by the cloud agent 350. For example, imaging protocol data is retrieved by the pull service module 362 from the device 232-236. Imaging protocol data can be retrieved directly from the device 232-236 (e.g., when the cloud agent 350 is integrated with and/or directly connected to the imaging device 232-236, etc.) and/or indirectly via the back-office network 452 (e.g., when a legacy imaging device 232-236 does not have the cloud agent 350 and the cloud agent 350 resides in the intermediary back-office network 452, etc.) via the pull service module 362 from the protocol database 368 of the imaging device 232-236.

At operation 1408, retrieved protocol(s) are relayed by the cloud agent 350 to the imaging protocol manager 310. For example, retrieved protocol information is routed by the file transfer 358 to the orchestration bucket 323 in the data store 321 of the imaging protocol manager 310. At operation 1410, the received protocol(s) are buffered at the imaging protocol manager 310 for processing. For example, each protocol can be assigned to a temporary folder in the orchestration bucket 323 to be retrieved for processing by the enricher 330 of the imaging protocol manager 310.

It should be understood that the protocol import process described with reference to FIG. 14 is for purposes of illustration only and not for limitation. Any suitable protocol import process with more, fewer, and/or different operations can be implemented to import protocols from imaging devices.

Figure 15:
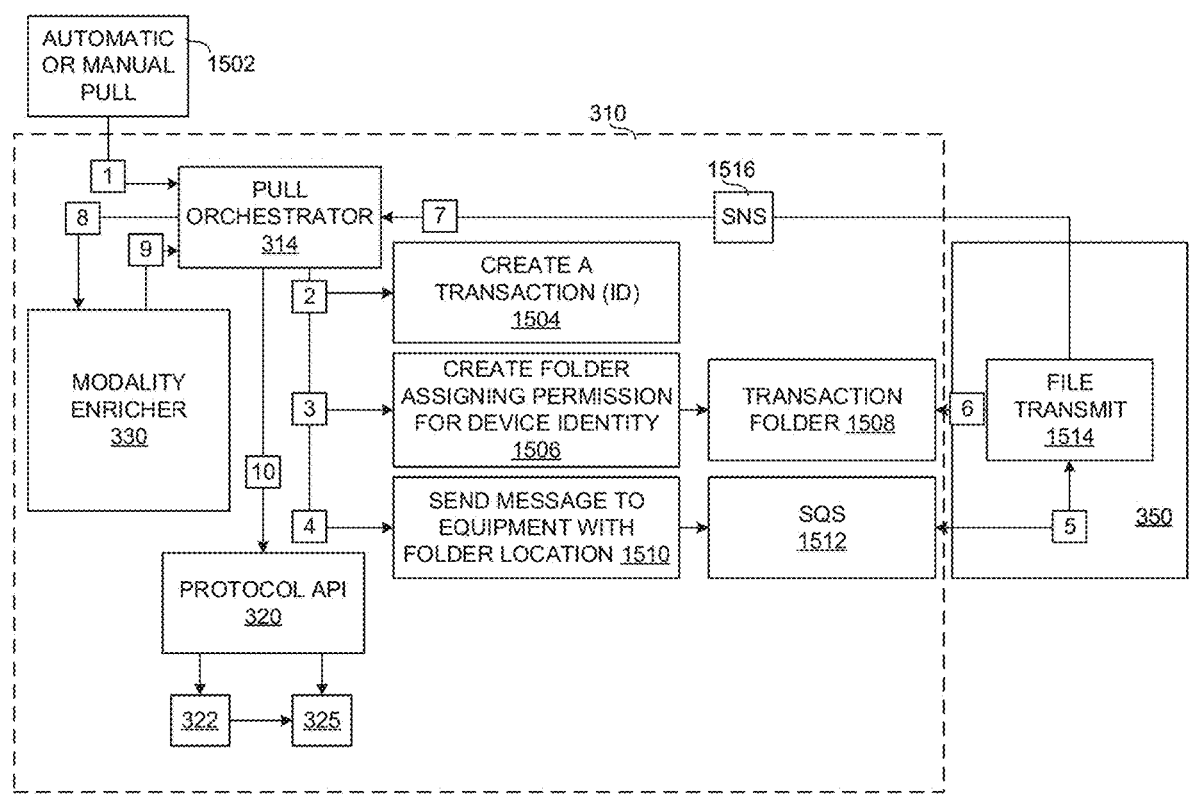
FIG. 15 illustrates a pull data flow of protocol information from an imaging device via the cloud agent to the imaging protocol manager of the example of FIG. 3, in accordance with an exemplary embodiment.

FIG. 15 illustrates an example pull data flow of protocol information from an imaging device 232-236 via the cloud agent 350 to the imaging protocol manager 310. The example pull flow is described as a sequence of activities 1-10. At 1, an automatic or manual pull 1502 initiates a protocol pull operation for the device 232-236 at the pull orchestrator 314 of the imaging protocol manager 310. At 2, the pull orchestrator 314 creates a transaction ID 1504 associated with the protocol pull operation from the device 232-236. At 3, the pull orchestrator 314 creates 1506 a folder assigning permission based on an identity of the device 232-236. The transaction folder 1508, stored in the orchestration bucket 323 can be named according to the transaction ID, for example. At 4, the pull orchestrator 314 sends a simple queue service (SQS) command 1512 to a corresponding equipment queue. At 5, the cloud agent 350 polls for a pull command. At 6, the cloud agent 350 uploads raw protocol information to the transaction folder 1508. At 7, the cloud agent 350 sends, via SNS 1516, a notification regarding completion of the protocol transaction. At 8, the pull orchestrator 314 calls the modality enricher 330 to generate a JSON object in the transaction folder 1508. At 9, the modality enricher 330 creates the JSON object for the raw protocol information and sends a completion event through SNS. At 10, the pull orchestrator 314 access the protocol API 320 to pull the protocol JSON object into the device protocol 322 and/or standards protocol 324 database and route protocol blob objects to a versioned bucket 325, for example.

It should be understood that the protocol intake process described with reference to FIG. 15 is for purposes of illustration only and not for limitation. Any suitable protocol input process with more, fewer, and/or different operations can be implemented to pull protocols from imaging devices.

Figure 16:
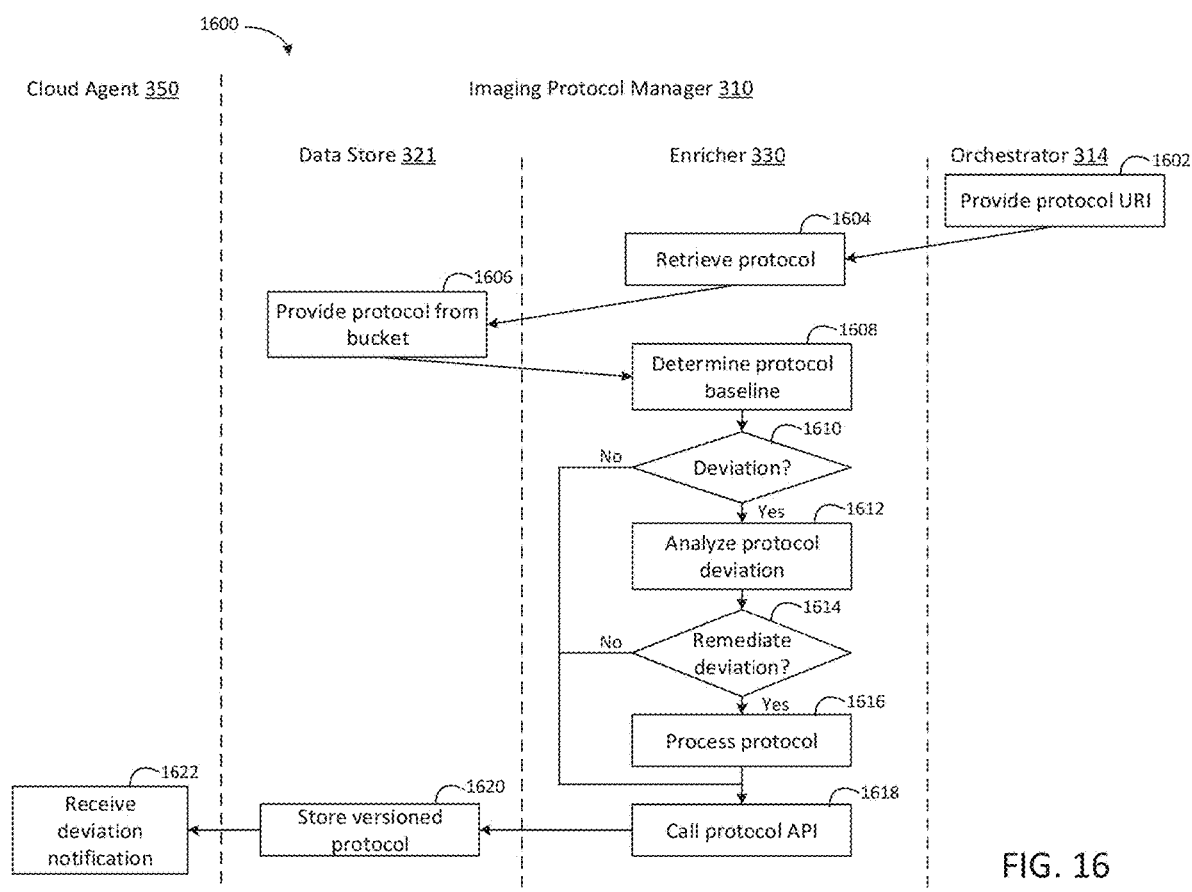
FIG. 16 provides further detail regarding implementation of an operation of the process of FIG. 9 to process protocols from an imaging device with the imaging protocol manager of the example of FIG. 3, in accordance with an exemplary embodiment.

FIG. 16 provides further detail regarding implementation of operation 906 to process protocols from an imaging device 232-236 with the imaging protocol manager 310, in accordance with an exemplary embodiment. At operation 1602, an indication of imaging protocol location (e.g., a URI for a folder in the orchestration bucket 323, etc.) is provided by the orchestrator 314 to the enricher 330. At operation 1604, the enricher 330 retrieves the protocol based on the locator. For example, the enricher 330 requests the protocol from the location of the folder in the bucket 323 of the data store 321. At operation 1606, the data store 321 provides raw protocol information from the orchestration bucket 323 to the enricher 330.

At operation 1608, the enricher 330 process the raw protocol data to determine a protocol baseline. For example, the baseline module 336 evaluates the protocol information in comparison to existing protocol information, such as a corresponding standard protocol 324. For example, protocol parameters, file size, file content, etc., can be compared between the incoming protocol information and existing protocol information stored in the device protocol library 322 and/or the standard protocol library 324.

At operation 1610, the protocol baseline results are evaluated to determine whether a deviation was identified. For example, the baseliner 336 of the enricher 330 analyzes the input protocol data in comparison to existing device protocol 322 and/or standard protocol 324 information to determine whether the protocol complies with an existing device protocol 322 (e.g., protocol previously evaluated with respect to the imaging device 232-236, etc.) and/or standard protocol 324 (e.g., a standard or normal protocol for the device type, application, etc.). If the protocols match, then the device 232-236 has a proper baseline. However, if the protocol information from the device 232-236 differs from the library 322, 324 information, then a deviation has been identified, for example.

If a deviation was identified, then, at operation 1612, the protocol deviation is analyzed. For example, the enricher 330 evaluates differences between stored and input protocol information. For example, a checksum can be used to compare a library protocol file with the input protocol file. If a difference in checksum reveals a deviation in the incoming protocol, then the incoming protocol information can be evaluated further to identify the deviation between protocols. For example, a parameter value can differ between the library protocol and the protocol pulled from the device 232-236. A sequence of actions or instructions can differ between the library protocol and the protocol pulled from the device 232-236, for example. By evaluating the contents of the protocol information, the deviation can be quantified and/or qualified, for example.

At operation 1614, to determine whether the deviation is to be remediated. For example, the deviation can be analyzed to determine whether the difference in the protocol pulled from the imaging device 232-236 is allowed under guidelines, rules, standards, etc. (e.g., safety guidelines, dosage limits, procedure best practices, etc.). A deviation against the rules, guidelines, standards, hospital practices, etc., can be a deviation to be remediated. However, the deviation can be a difference in protocol preferred by a clinician, practice, organization, etc. Such deviations may not be remediated. Instead, the protocol can replace existing protocol information and/or be stored as a new version of an existing protocol, for example.

If the deviation is to be remediated, then, at operation 1616, the protocol is processed. For example, the pulled protocol information is processed to replace the pulled protocol with a stored protocol from the device protocol 322 and/or standard protocol 324 library (e.g., including clinical instructions 328). In some examples, the protocol can be corrected based on the difference(s) identified at operation 1612.

At operation 1618, the protocol API 320 is called. The protocol API 320 can update the library(-ies) (e.g., the standards protocol library 324, device protocol library 322, clinical instructions 326, etc.). If an updated or new protocol (or protocol version) is to be stored in the device 322 and/or standard 324 protocol library, the protocol API 320 facilitates the update. Alternatively or in addition, the protocol API 320 can trigger storage of protocol information in the versioned bucket 325, such as by device 323-326 and protocol version, etc. At operation 1620, the protocol information is stored (e.g., in the library(-ies) 322-326 and/or the version bucket 325, etc.).

At operation 1622, the cloud agent 350 can (optionally) receive a notification of protocol update and/or deviation. For example, if a protocol pulled from the imaging device 232-236 needs to be replaced, the imaging protocol manager 310 can trigger a message to the cloud agent 350 so that the cloud agent 350 is ready to provide an updated/replacement protocol to the device 232-236. In some examples, even if no protocol repair/replacement is indicated, the cloud agent 350 can receive confirmation of protocol processing and storage (e.g., including an identifier and/or other indicator for future protocol reference, etc.).

It should be understood that the protocol processing described with reference to FIG. 16 is for purposes of illustration only and not for limitation. Any suitable process with more, fewer, and/or different operations can be implemented to process clinical protocols from imaging devices with the protocol manager.

Figure 17:
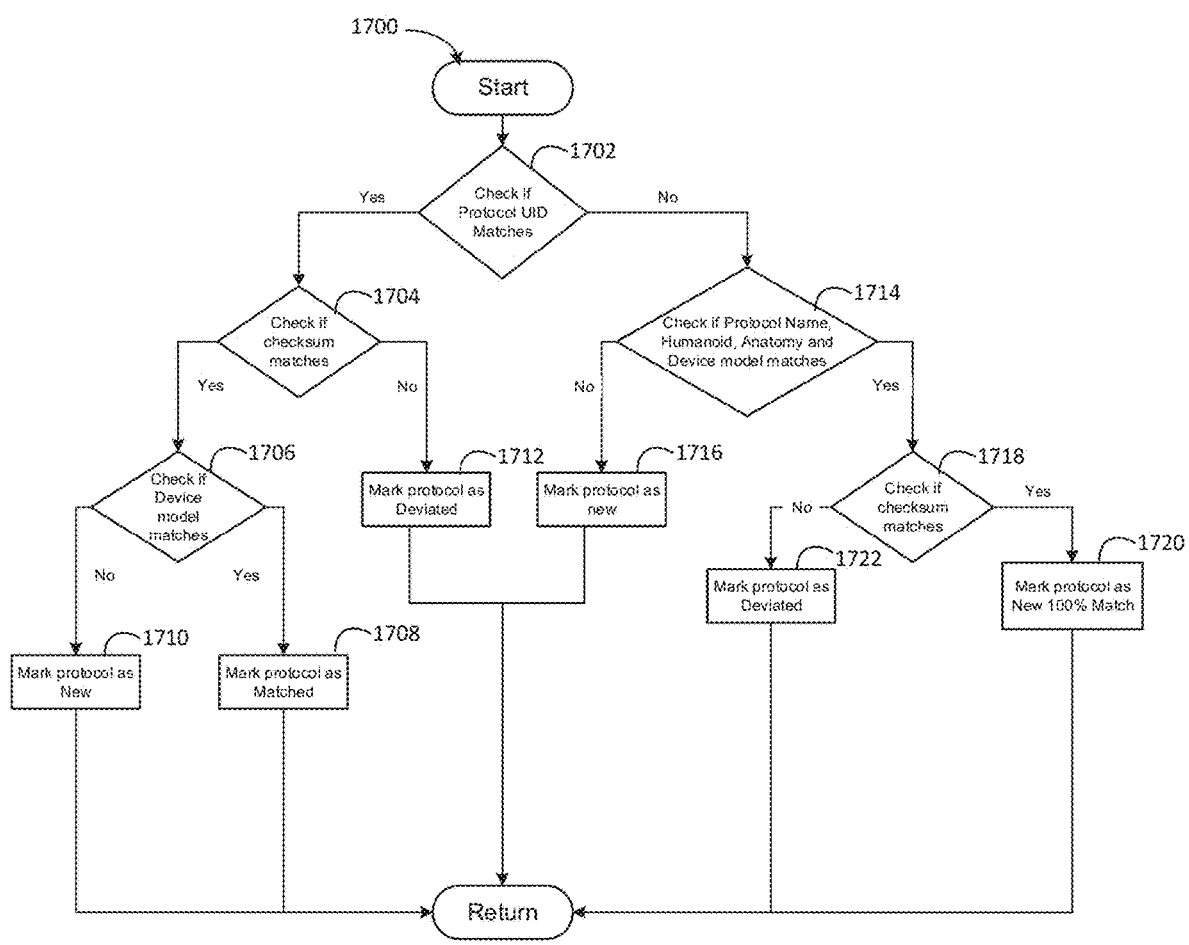
FIG. 17 provides further detail regarding implementation of an operation of the process of FIG. 9 to process a protocol from an imaging device with the imaging protocol manager of the example of FIG. 3 to determine a protocol baseline, in accordance with an exemplary embodiment.

FIG. 17 provides further detail regarding an example implementation of operation 1608 to process a protocol from an imaging device 232-236 with the imaging protocol manager 310 to determine a protocol baseline. At operation 1702, protocol identifiers (e.g., universal identifiers or UIDs, etc.) are evaluated to determine whether the identifiers match. For example, UIDs for a protocol pulled from an imaging device 232-236 and a stored protocol 322, 324 are compared to determine whether or not the UIDs match.

If the identifiers match, then, at operation 1704, a checksum and/or other data integrity calculation is performed on the library 322, 324 protocol file and the pulled protocol file from the imaging device 232-236. If the checksums match, then, at operation 1706, a model of the device 232-236 from which the protocol was pulled is compared to a device model associated with the library protocol. If the device models match, then, at operation 1708, the protocol is marked as matched. In certain examples, a matched protocol is not available for further review by a user (e.g., via the workstation 1002, etc.) because a match to the protocol is already available in the library 322, 324.

However, if the device models do not match, then, at operation 1710, the imported protocol is marked as new. That is, since the checksum matches but the device model does not match, the protocols are likely similar, but not identical, protocol versions. In some examples, the imported protocol is assigned a new protocol UID as the protocol is moved into the library 322, 324 during baseline commit to avoid protocol UID duplicates across models. In some examples, the protocols can exist as different versions of the same protocol in the library(-ies) 322, 324 and/or versioned buckets 325 of the data store 321.

If, at operation 1704, the checksums do not match, then, at operation 1712, the imported protocol is marked as deviated. For example, since the identifiers match but the checksums differ, the imaging protocol manager 310 determines that a deviation in the identified protocol has occurred in the imported protocol. The protocol is marked or flagged for further analysis/processing.

If, at operation 1702, the protocol identifiers do not match, then, at operation 1714, the protocol is further analyzed to determine whether protocol name, humanoid, anatomy and device model matches. For example, meta data associated with the protocol is processed to determine whether protocol name, humanoid, anatomy and device model matches between the library protocol and the imported protocol. If there is no match, then, at operation 1716, the protocol is marked as new.

However, if the information matches, then, at operation 1718, a checksum and/or other data integrity calculation is performed on the library 322, 324 protocol file and the imported protocol file pulled from the imaging device 232-236. If the checksums match, then, at operation 1720, the protocol is marked as a new match (e.g., new 100% match, etc.). However, if the checksums do not match, then, at operation 1722, the protocol is marked as deviated.

It should be understood that the protocol baselining process described with reference to FIG. 17 is for purposes of illustration only and not for limitation. Any suitable process with more, fewer, and/or different operations can be implemented to perform a baselining and deviation analysis with respect to protocols imported from imaging devices.

Thus, as described above, device protocols can be stored in a dedicated folder and/or other location (e.g., versioned bucket 325 of the example of FIG. 3) created for each imaging device. Device protocols in the cloud are identified via a unique protocol ID and can be reviewed, compared, retrieved, and provided to imaging devices 232-236 via the imaging protocol manager 310 in conjunction with the cloud agent 350. In certain examples, a revision history is available via the imaging protocol manager 310 (e.g., a copy of the protocol with version number, etc.). Different versions of a device protocol can be tracked and organized separately for download to different models of a device type, for example. When a device protocol is first pulled into the imaging protocol manager 310, the protocol is assigned a globally unique ID and tagged as Version 1, for example. On subsequent pulls, if the protocol's content changes on the device 232-236, a new object is added with an incremented version number (e.g., Version 2), for example.

The data store 321 provides an orchestration bucket 323 and a versioned bucket 325 of protocol information. For each request from the imaging protocol manager 310 to a device 232-236 for protocol interaction with the device 232-236 (e.g., pull and/or push via the cloud agent 350, etc.), a unique transaction identifier (ID) is generated and associated in the orchestration bucket 323. The protocol(s) uploaded from the device 232-236 to the imaging protocol manager 310 are stored in a transaction folder in the orchestration bucket 323 that is unique per transaction. The transaction folder can be temporary for the duration of the transaction and/or more permanently associated with a device, device type, etc. Protocols stored on the imaging protocol manger 310 can be stored as a protocol library in the versioned bucket 325 of the data store 321. Protocols stored in the versioned bucket 325 can be stored in the same format/structure as the corresponding protocols executing on the imaging device 232-236, for example.

Pulling or other import of clinical device protocols from imaging devices 232-236 can vary according to system configuration, modality, environment, etc. For example, protocol pulling can occur when the imaging device 232-236 (e.g., a CT scanner, etc.) is idle, rather than occurring during an active scan by the device 232-236. In certain examples, the cloud agent 350 can determine whether or not the device 232-236 is in operation and initiate pulling of protocol information from the device 232-236 to the imaging protocol manager 310 when the device 232-236 is idle. In other examples, pulling of protocol information can occur during a scan. For example, in an MR machine, protocol data being pulling is relatively small and pulling does not disturb a scanning session.

As described above, the cloud agent 350 can actively poll for commands in the request queues. When a command is received from the cloud-based imaging protocol manager 310, the imaging device 232-236 can validate the command and take corresponding action. Request queues can be created per device 232-236 via the command and notifications module 317 in the imaging protocol manager 310 to send polling request commands to the command and notification API 356 of the cloud agent 350 for the device 232-236. A response queue is used to receive messages from the equipment 232-236 back to the command and notification API 356 of the imaging protocol manager 310. Such messages can indicate completion and/or failure of execution of a command by the equipment 232-236 to pull protocol information from the protocol database 368, etc.

In certain examples, the push/pull orchestrator 314 can perform additional services such as concurrency management, monitoring and publishing job status, detecting duplication, versioning objects, and storing protocols in versioned buckets 325. The orchestrator 314 provides raw protocol URIs to the enricher 330. The enricher 330, which may be modality-specific, is responsible for calling modality-specific functions to convert raw protocols to JSON format in the cloud-based imaging protocol manager 310. Since protocols from different devices (e.g., different scanner models, etc.) can be maintained in different formats, the data stored and processed in the imaging protocol manager 310 is converted to a single JSON format for processing (e.g., baselining, deviation processing, etc.). Clinical instructions 326 associated with protocols 322, 324 can be pulled from imaging devices 232-236 and maintained in the imaging protocol manager 310, for example.

Via a web-based portal and/or other application (e.g., running on the workstation 1002 enabled by the web host 318, etc.), a user, application, and/or other system can review a status of protocol pulling, such as: "Pulling in progress" "Failed: pulling failed," "Completed: pulling completed," etc. One or more logs/reports can be maintained to track what protocols are pulled, who is pulling the protocols, what protocols are edited, etc.

In certain examples, a user, application, and/or system can mark certain protocols pulled from imaging devices 232-236 as "standard" protocols. The user/application/system can create a protocol library in the standard protocols database 324 to publish the standard protocols, for example. Before committing a protocol to the library, the protocol manager 310 performs a baselining process 336 (e.g., via the baselining process of FIGS. 16-17, etc.) to determine whether the protocol matches and/or deviates from an existing protocol 322, 324 in the library. Via the web-based portal/application enabled by the protocol application 318, the user/application/system can create and manage the protocol library, have protocols baselined, mark standard protocols, and publish protocols in the library, for example.

In the standard protocols database 324 (e.g., forming and/or including in the protocol library), a storage area is created for a group of devices across which the protocols are compatible. The storage area enables pulling and pushing of protocols across the group of devices. In some examples, the grouping of devices is created using a device model and software version, and each compatible group is given a unique model UID. There can be multiple models that are mapped to the same model UID. For example:

| Model | Software Version | Model UID |
| --- | --- | --- |
| LightSpeed | 07MW_11.0 | ModelUID_1 |
| LightSpeed | 07MW_12.0 | ModelUID_1 |

The UID can be used to select applicable enricher 330 components for baseline grouping, identifying applicable devices to push protocols, etc. Clinical protocols can be organized in one or more hierarchies in the standard protocols database 324 of the imaging protocol manager 310. Baselining can be applied to protocol groupings, individual protocols, etc.

Via the web-based portal/application (e.g., on the workstation 1002, etc.) enabled by the web host 318, the user can view the status of baselining and outcome of baselining for the protocols, such as "Review: protocol review in progress," "Deviation compute: library update in progress," "Completed: library updated successfully," "Cancelled: cancelled by user,", etc. The application/portal (e.g., accessible via the workstation 1002, etc.), a user can browse, view, edit, search, compare, etc., stored protocols via the protocol application 318, for example. For example, the user can browse device protocols in the device protocols database 322 and standard protocols in the library 324 (as well as clinical instructions 326).

The user can also view recent updates to check for new, modified, and/or deleted protocols, for example. The user can rename, version, and/or otherwise arrange protocols in the cloud-based imaging protocol manager 310, for example. The user can search protocols in the device protocols database 322 and/or the standard protocols database 324 by name, body part, anatomy, age (e.g., pediatric versus adult), patient size, etc. The user can compare two or more protocols including, for example, versions of device protocols, versions of library protocols, first device protocol versus second device protocol, device protocol versus standard library protocol, library standard protocol versus library standard protocol, etc. Deviation can be tracked via baselining and comparison, for example.

These and/or other external applications (e.g., external application(s) 250, etc.) can leverage the imaging protocol manager 310. The protocol API 320 provides the interface for external applications to access the protocol manager 310, for example.

Figure 18:
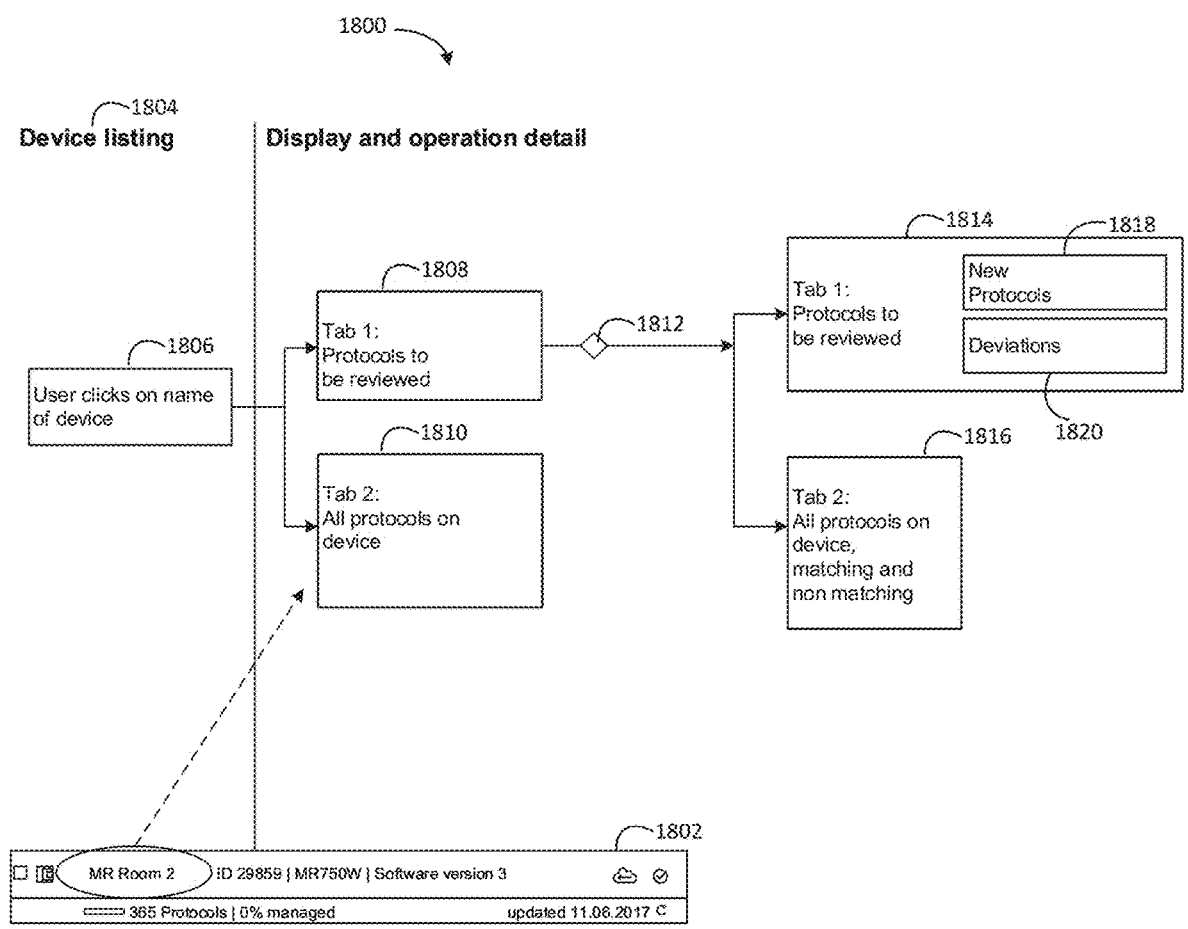
FIG. 18 illustrates a process flow and interaction via a web portal and/or other application accessible via the computing device of the example of FIG. 10, in accordance with an exemplary embodiment.

FIG. 18 illustrates an example process flow and interaction 1800 via a web portal and/or other application 1802 such as accessible via the workstation 1002. From a device listing 1804, a user can select 1806 an imaging device 232-236. Selecting the device triggers a display of a plurality of tabs 1808, 1810 via the portal/application 1802. A first tab 1808 shows protocols to be reviewed, and a second tab 1810 shows a list or other set of all protocols on the selected imaging device 232-236, for example. From the set of protocols to be reviewed in the first tab 1808, a baselining operation 1812 can be triggered. For example, the user can select one or more protocols and one or more libraries for baseline comparison, and imaging protocol manager 310 executes the baseline operation 1812. A plurality of tabs 1814, 1816 are generated in the portal/application graphical user interface 1802 as a result of the baselining operation 1812. A first tab 1814 shows protocols be reviewed as a result of the baselining 1812, and a second tab 1816 shows all protocols on the device 232-236 and an indication of whether the protocol is matching or non-matching to the library 322, 324, for example. In the first tab 1814, protocols to be further reviewed can be identified as new protocols 1818 and deviations 1820, for example. Thus, a user can navigation the portal/application interface 1802 to view, review, and interact with protocols and associated protocol analysis, for example.

Figure 19:
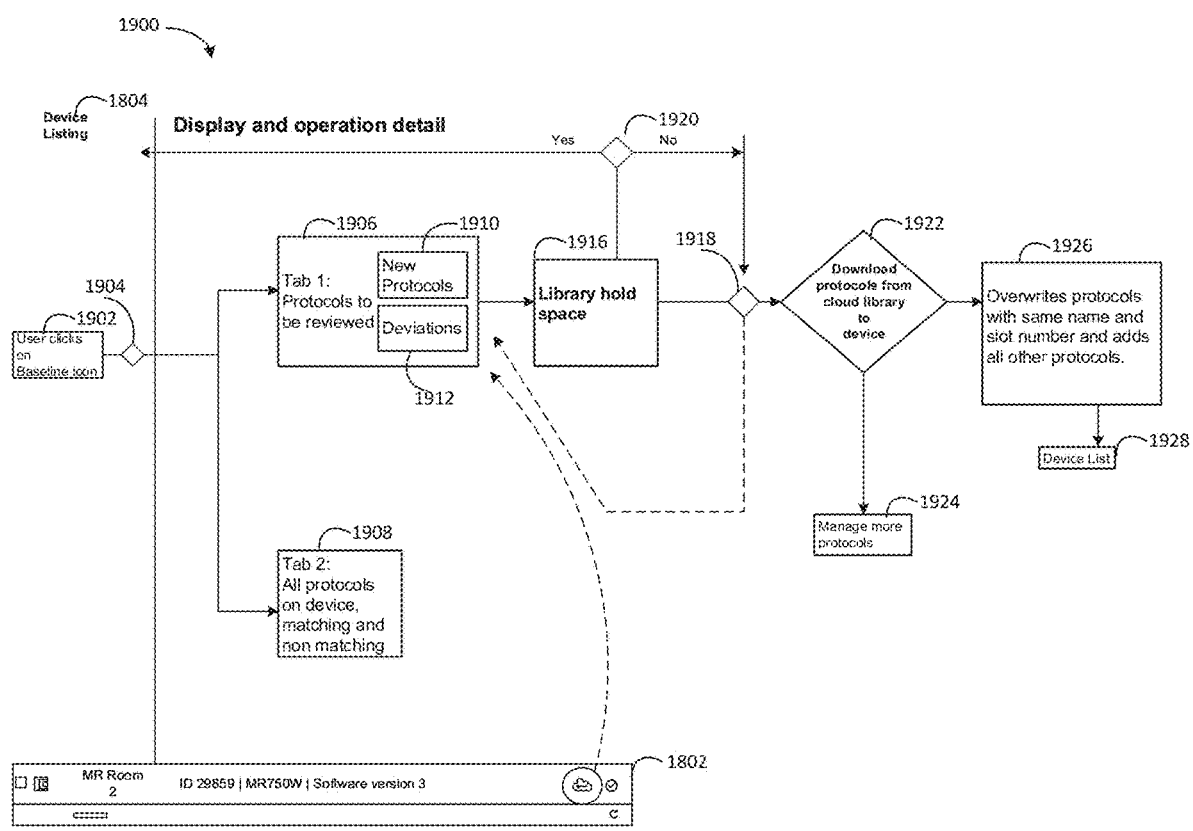
FIG. 19 illustrates another process flow and interaction via the web portal and/or other application accessible via the computing device of the example of FIG. 10, in accordance with another exemplary embodiment.

FIG. 19 illustrates another example process flow and interaction 1900 via the web portal and/or other application 1802 such as accessible via the workstation 1002. From the device listing 1804, a user can select 1902 a baseline icon to trigger a baseline operation 1904 to compare imported protocol(s) against library protocols stored by the imaging protocol manager 310. Following completion of the baseline operation 1904, results are displayed in multiple tabs 1906, 1908 of the portal/application 1802. As shown in the example of FIG. 19, a first tab 1906 can display results of the baselining 1904 including new protocols 1910 and identified deviations 1912.

For new protocols 1910, a plurality of actions can be facilitated via the portal/application 1802. For example, a new protocol can be added to a library 322, 324 and/or to a versioned bucket 325 folder. Clinical instructions 326 can be added. The new protocol can be copied, compared, etc. The protocol name editor 342 can also be called to edit the protocol name. For a deviation 1912, the deviating protocol can be added to a library 322, 324 and/or to a versioned bucket 325 folder. Clinical instructions 326 can be added. A deviating protocol can be made a standard protocol 322, compared to a standard protocol 322, copied, etc. The protocol name editor 342 can also be called to edit the protocol name.

If a protocol is to be added to a database 322, 324, the protocol is moved to a library holding space or buffer 1916. At 1918, the protocol can be committed to a library 322-326. Via the library holding space 1916, a protocol can be deleted, moved to a folder 325, made standard, name edited, clinical instructions added, etc. After a protocol is committed, control can revert back to the tab 1906 to manage additional protocol(s), for example. Additionally, at 1920, the library 322, 324 is evaluated to determine whether the library has been updated. If the library 322, 324 has been updated, then control reverts back to the device listing 1804. If the library 322, 324 has not been updated, then the library 322, 324 can be synchronized (e.g., with the holding or staging area 1916, etc.) and/or additional protocol(s) can be managed at 1918, for example.

At 1922, one or more protocols can be downloaded to one or more imaging device(s) 232-236 from the library(-ies) 322-326. If protocol(s) have been downloaded, then, at 1924, additional protocol(s) can be managed via the interface 1802. If protocols are to be downloaded, at 1926, protocol(s) with the same name and slot number are overwritten and other protocol(s) are added. In certain examples, protocol(s) with a slot number not covered by the library 322, 324 are "unmanaged" on the device 232-236. At 1928, the device list 1804 is updated.

Example Protocol Distribution Systems and Methods

As discussed above, the standard protocols database 324 maintains one or more protocol libraries that publish protocols marked as "standard" by the user(s). The published standard protocols can be distributed (i.e., pushed) to compatible imaging devices across the organization. When a protocol is marked as standard and committed to the library, metadata of the protocol is automatically adjusted to strip certain data specific to the imaging instance. In other words, a standard protocol published in the library does not contain metadata specific to the imaging device on which it was created and developed, but contains metadata to identify models with which the protocol is compatible and metadata to identify the scenario/task the protocol is for.

Figure 20:
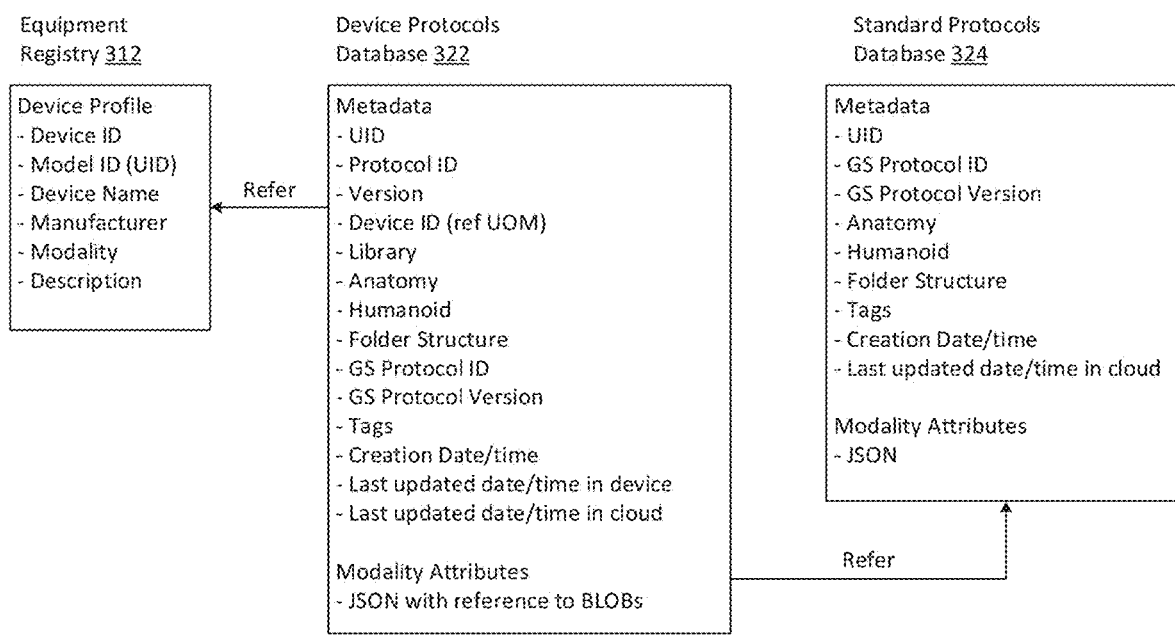
FIG. 20 is a structure of metadata for protocols in the device protocol database and the standard protocols database, in accordance with an exemplary embodiment.

Referring to FIG. 20, a comparison of metadata for device protocols and metadata for standard protocols is shown, in accordance with an exemplary embodiment. As shown in FIG. 20, in some embodiments, the metadata associated with a protocol pulled from an imaging device and stored in the device protocols database 322 includes the model ID (i.e., UID), protocol ID in the device, protocol version in the device, device ID, library associated with the protocol, anatomy, humanoid, folder structure in the device, global system (GS) protocol ID, GS protocol version, tags attached to the protocol, data/time when the protocol was created, last updated date/time in the device, last updated data/time in cloud, etc. The metadata associated with a protocol marked as standard and published in the library includes: UID, GS protocol ID, GS protocol version, anatomy, humanoid, folder structure in the library, tags, date/time when the protocol was created, last updated date/time in the cloud, etc. In some embodiments, the device protocol database 322 refers to the equipment registry 312 for information on the device and to the standard protocols database 324 for GS protocol ID and version.

A process of pushing protocols is illustrated in detail with reference to FIGS. 3 and 21, according to an exemplary embodiment. In some embodiments, a user may request to distribute one or a set of standard protocols via the web-based portal/application enabled by the web host 318. For example, the user may select the protocol(s) to be pushed from a user interface (e.g., GUI) provided by the web-based portal/application. The user should have permission to push protocols. In some embodiments, the user is authenticated before being able to push any protocol. In some embodiments, the user can push an entire library to a device at one click, provided that every protocol in the library is compatible with the device. For example, the user interface may include a button/icon/menu item of "Push Entire Library." The user may click on it to indicate pushing the entire library. In some embodiments, the user can schedule the distribution to devices. For example, the user may indicate, via the user interface, a time when he/or she wants the distribution to happen. In some embodiments, one or a set of standard protocols may be automatically distributed by the protocol manager 310. For example, when a new standard protocol or a new version of standard protocol is published in the library, the protocol manager 310 may determine to distribute the protocol to compatible devices. As another example, the protocol manager 310 may automatically distribute standard protocols periodically (e.g., daily, weekly, etc.).

Figure 21:
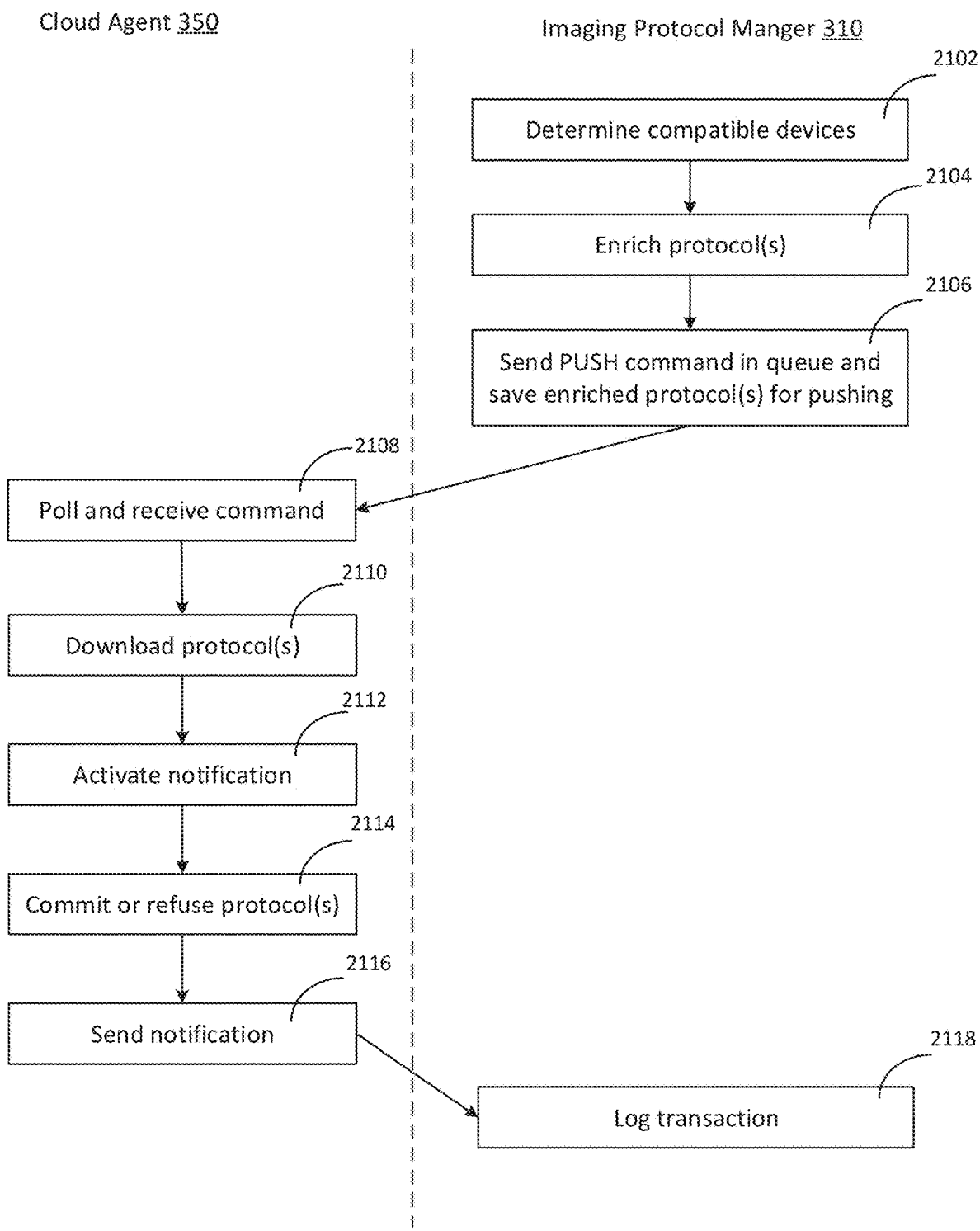
FIG. 21 provides further detail regarding implementation of an operation of the process of FIG. 9 to push protocols to an imaging device with the imaging protocol manager via the cloud agent of the example of FIG. 3, in accordance with an exemplary embodiment.

Referring to FIG. 21, a dashed line is used to schematically separate operations performed by the cloud agent 350 and operations performed by the image protocol manager 310. At operation 2102, devices that are compatible with the protocol(s) to be pushed are determined by the compatible checker 344 at the imaging protocol manager 310. As discussed above, metadata for a published protocol includes a model ID (i.e., UID). Each UID is given to a compatible group of imaging devices. There can be multiple models that are mapped to the same model UID. The equipment registry 312 maintains a device profile for each registered device, which includes a UID that identifies the compatible group to which the device belongs. The compatibility checker 344 identifies the UID in the metadata for the protocol to be pushed and determines that the imaging devices with the same UID are compatible devices. In some embodiments, a list of all compatible devices is displayed at the user interface for the user to confirm or further select. In some embodiments, the list of all compatible devices is returned to the push/pull orchestrator 314.

At operation 2104, the protocol(s) to be pushed is enriched by the push enricher 334 at the protocol manager 310. The push enricher 334 performs a reverse process of the pull enricher 332. As discussed above, the pull enricher 332 converts raw protocols from imaging devices to JSON format to store in the cloud. The push enricher 334 calls appropriate modality-specific functions to convert the JSON format to raw protocols used by imaging devices according to the uniform resource identifier (URI) associated with the devices.

At an operation 2106, the pull/push orchestrator 314 sends a PUSH command in the command queue 317A and saves the enriched protocol(s) at a folder associated with the transaction in the orchestration bucket 323. For example, the orchestrator 314 creates a unique transaction identifier (ID) for a transaction of pushing protocol(s) to a device, which can be used to associate the transaction with the folder in the orchestration bucket 323. In some embodiments, there are various types of PUSH commands, including, for example, Replace All, Add New, Modify Existing, or Delete, each PUSH command being associated with a list of protocol(s). The Replace All command requests replacing all existing protocols in the protocol database 368 used by the imaging device with a list of protocols associated with the command. The Add New command requests adding a list of protocols associated with the command to the protocol database 368 of the device. The Modify Existing command requests modifying corresponding protocol(s) in the protocol database 368 of the device with a list of protocol(s) associated with the command. The Delete command requests deleting a list of protocol(s) associated with the command from the protocol database 368 of the device. In some embodiments, the use selects a type of PUSH command from a user interface (e.g., GUI) provided by the web-based portal/application enabled by the web host 318. In some embodiments, the push/pull orchestrator 314 determines a command type automatically.

At operation 2108, the command and notification API 356 at the cloud agent 350 polls for commands in the command queue 317A of the command & notification module 317 and receives the PUSH command placed by the push/pull orchestrator 314. As discussed above, the command and notification API 356 polls the command queue 317 at an interval. When one or more PUSH commands are placed during the interval, the command and notification API 356 receives the one or more commands.

At operation 2110, the file transfer SDK 358 at the cloud agent 350 downloads protocol(s) from the folder associated with the PUSH transaction from the orchestration bucket 323. In some embodiments, the cloud agent 350 includes a staging area (not shown in FIG. 3) that stores the downloaded protocol(s).

At operation 2112, the file transfer SDK 358 activates the push service module 364 at the cloud agent 350. The push service module 364 checks the status of the imaging device and activates a notification based on the device status. In some embodiments, an imaging device allows processing the transaction while scanning. In some embodiments, an imaging device does not allow processing the transaction while scanning. When the imaging device is capable of processing PUSH transactions, the notification may be activated for the review by a technician or clinical specialist responsible for the operation of the imaging device. The notification can be provided via a user interface (e.g., GUI) displayed at the imaging device or a workstation associated with the imaging device. In some embodiments, the notification includes a list of incoming PUSH command(s), the type of each command, and a list of protocol(s) associated with each command for the technician or clinical specialist to review. In some embodiments, the notification prompts the technician or clinical specialist to accept or reject the transaction. For example, the user interface may include a button/icon/menu item of "Accept." The technician or clinical specialist may click on it to indicate that the transaction is accepted. The user interface may include a button/icon/menu item of "Reject." When "Reject" is indicated, the user interface may further prompt the technician or clinical specialist to input a valid business and/or clinical reason for the rejection.

If more than one PUSH commands are received from the cloud, the commands can be accepted or rejected in the same order as in the command queue 317A so that no protocols are discarded or overridden by mistake. However, in some embodiments, if a Replace All command is the most recent command, the technician or clinical specialist is allowed to accept this command before any earlier command. Accepting this command would automatically reject all earlier commands with the reason of being overridden by a Replace All command.

At an operation 2114, the protocol(s) at the staging area is committed to or refused to be committed to the protocol database 368 of the imaging device, depending on whether the transaction is accepted or rejected by the technician or clinical specialist. If the technician or clinical specialist indicates to accept the transaction in the notification, the commit service module 366 moves the protocol(s) associated with the transaction to the protocol database 368, which now becomes protocol(s) that can be used by the imaging device. If the transaction is Replace All, all existing protocols in the protocol database would be replaced. If the transaction is Add New, the protocol(s) would be added to the protocol database 368. If the transaction is Modify, corresponding protocol(s) in the protocol database 368 would be modified by the protocol(s). If the technician or clinical specialist indicates to reject the transaction in the notification, the associated protocol(s) would not be committed to the protocol database 368 of the imaging device.

In some embodiments, the system of the imaging system may need to be rebooted in order to apply the changes of protocols. The push service module 364 may activate a notification that reboot is required to apply the changes of protocols.

In some embodiments, the technician or clinical specialist might want to "undo" an accepted transaction. For example, the user interface may include a button/icon/menu item of "Undo." The technician or clinical specialist clicks on it to indicate to undo an accepted transaction. The commit service module 366, before committing any protocol to the protocol database 368, backs up a list of protocol(s) to be affected by the transaction. An Undo action would restore the backup list of protocol(s) to the protocol database 368.

In some embodiments, the user may want to cancel the PUSH transaction from the end of the cloud via the user interface enabled by the web host 318. If the cloud agent 350 receives the command of cancel after the protocol has been committed to the protocol database 368, the transaction cannot be canceled. If the cloud agent 350 before the command of cancel, the commit service module 366 would not commit the protocols to the database 368.

At operation 2116, the command and notification API 356 sends a notification to the notification queue 317B of the command & notification module 317. For example, if the transaction is accepted and successfully performed at the cloud agent 350 (e.g., being committed), the message may indicate success of the transaction. If the transaction is rejected or failed to be committed for other reasons, the message may indicate failure of the transaction and optionally the reason of failure. In some embodiments, the command and notification API 356 may send notification(s) to indicate success or failure of various steps throughout the transaction. For example, a notification may indicate the success or failure of downloading the protocol(s) from the cloud to the staging area of the cloud agent 350 when the operation 2110 is performed.

At operation 2118, the PUSH transaction is logged by the push/pull orchestrator 314. The logged information may include, for example, what protocols were pushed for the transaction, who pushed the protocol(s), timestamps of when the transaction was created and/or when the transaction was done, status of transaction (e.g., success or failure), etc.

In some embodiments, the process of the PUSH transaction is monitored by the protocol manager 310 and displayed at a user interface provided by the web-based portal/application enabled by the web host 318. Thus, a user can see where a particular protocol is distributed to and the progress of the distribution. For example, the user interface may indicate the PUSH transaction being "Started," "Protocols being processed," "Protocols being downloaded," "Reboot pending," "Protocol being committed to device," "Cancel success," "Cancel failed," and so on.

Figure 22A:
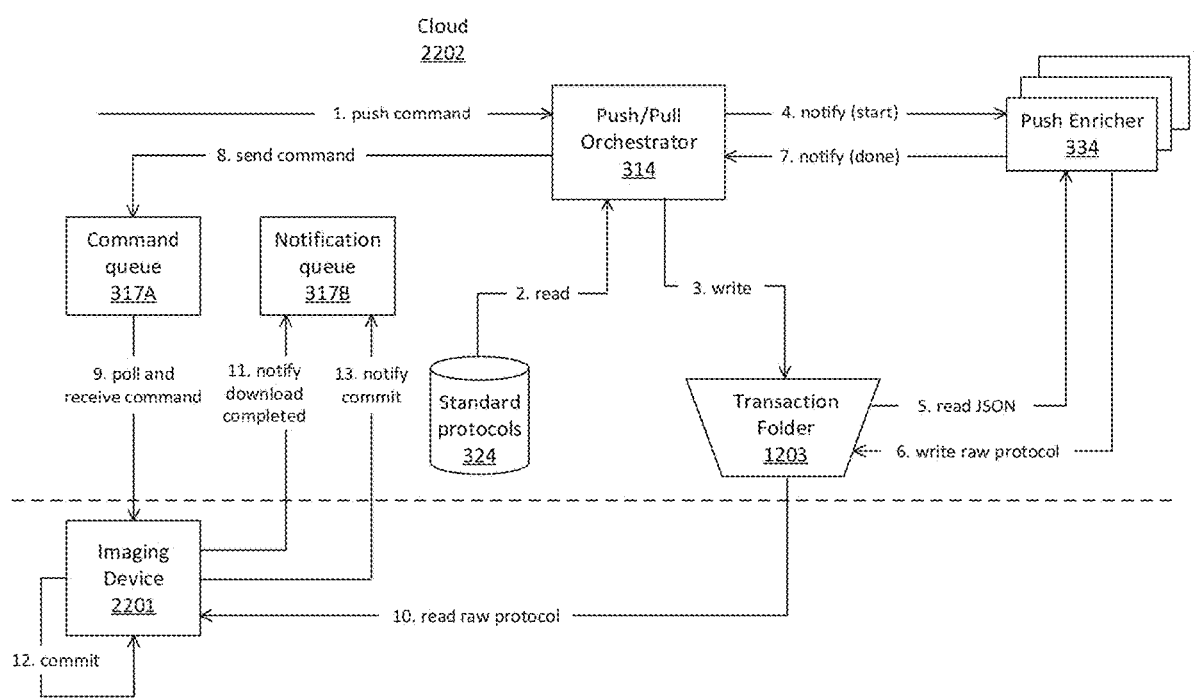
FIG. 22A illustrates a push data flow from the perspective of the image protocol manager, in accordance with an exemplary embodiment.

Referring to FIG. 22A, a push data flow from the perspective of the image protocol manager is shown, in accordance with an exemplary embodiment. A dashed line is used to schematically separate the imaging device 2201 side and the cloud 2202 side. Components of the imaging protocol manager 310 are located in the cloud 2202. Cloud agent 350 is on the imaging device 2201 side. In some embodiments, the protocol manager 310 is aware of interactions with the device side but not of operations performed at the device side internally.

At 1, the push/pull orchestrator 314 receives a PUSH command that may identify, for example, protocol(s) associated with the transaction and the device for the transaction. The orchestrator 314 may create a unique ID for the transaction. At 2, the orchestrator 314 reads the protocol(s) associated with the transaction from the standard protocols database 324. At 3, the orchestrator 314 writes the protocol(s) to a transaction folder 1203 associated with the transaction ID in the orchestration bucket 323. At 4, the orchestrator 314 notifies the push enricher 334 to start to enrich the protocol(s). At 5, the push enricher 334 reads the protocol(s) in the JSON format from the transaction folder 1203. At 6, the push enricher 334 converts the JSON format to raw protocol(s) for the device and writes the raw protocol(s) to the transaction folder 1203. At 7, the push enricher 334 notifies the orchestrator 314 that the enriching is done. At 8, the orchestrator 314 sends the command (identified by the transaction ID) to the command queue 317A. At 9, the command in the queue 317A is polled and received by the imaging device 2201 side. At 10, raw protocol(s) associated with the transaction are downloaded from the transaction folder 1203 to the device 2201 side. At 11, the notification queue 317B receives a notification from the device 2201 side indicating that download is completed. At 12, the protocol(s) are committed at the device 2201 side. At 13, the notification queue 317B receives a notification from the device 2201 side indicating success of committing.

Figure 22B:
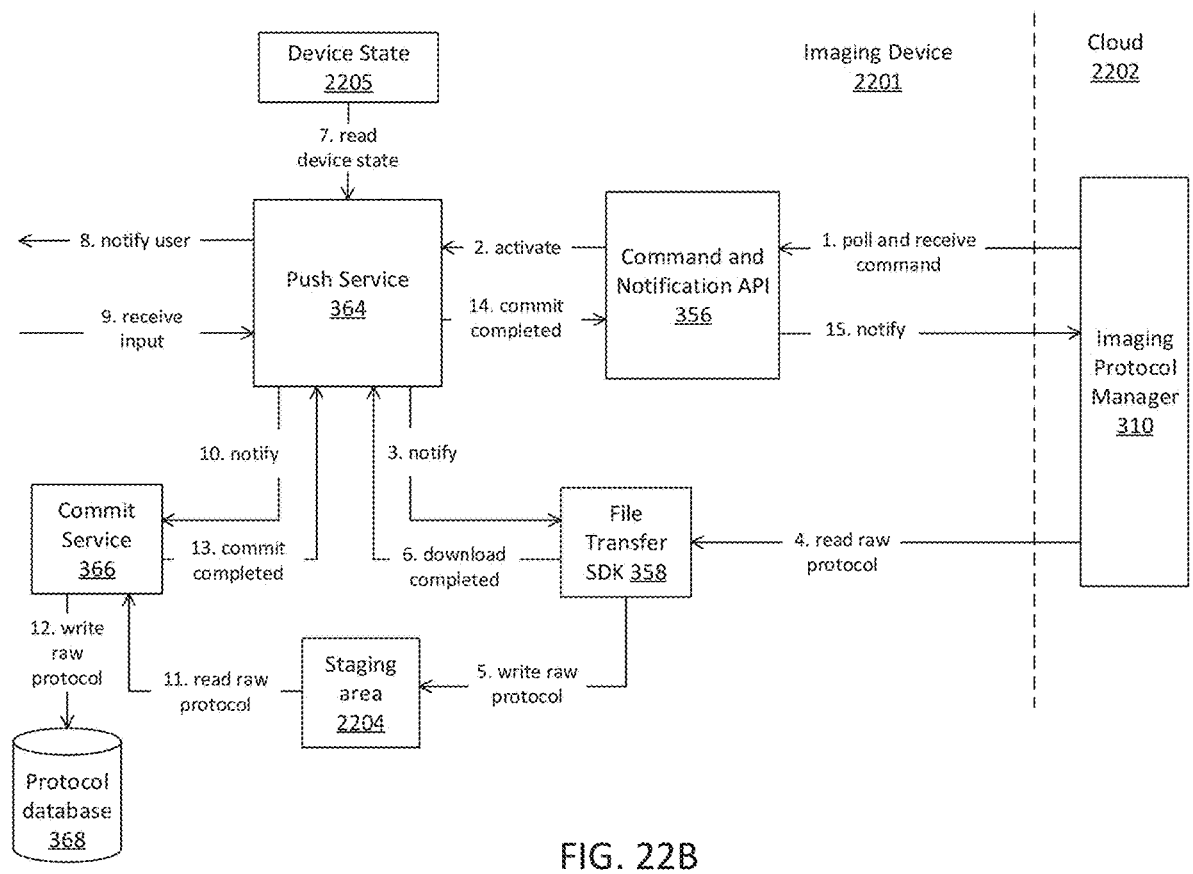
FIG. 22B illustrates a push data flow from the perspective of the imaging device, in accordance with an exemplary embodiment.

Referring to FIG. 22B, a push data flow from the perspective of the imaging device 2201 (or the cloud agent 350) is shown, in accordance with an exemplary embodiment. A dashed line is used to schematically separate the imaging device 2201 (or the cloud agent 350) side and the cloud 2202 (or the protocol manager 350) side. In some embodiments, the imaging device 2201 (or the cloud agent 350) side is aware of interactions with the cloud 2202 side but not of internal operations in the cloud.

At 1, the command and notification API 356 polls and receives the PUSH command from the cloud 2202 side. At 2, the command and notification API 356 activates the push service module 364. At 3, the push service module 364 notifies the file transfer SDK 358 to download raw protocol(s) associated with the command from the cloud 2202 side. At 4, the file transfer SDK 358 reads raw protocol(s) from the cloud 2202 side. At 5, the file transfer SDK 358 writes the raw protocol(s) to a staging area 1204. At 6, the file transfer SDK 358 notifies the push service module 364 that the download is completed. At 7, the push service module 364 reads the device state from a device state checker or a device state storage 2205. If the device is in a state ready for the transaction, then at 8, the push service 364 notifies a technician or clinical specialist of the transaction. At 9, the push service 364 receives the user input regarding accepting or rejecting the transaction. If the transaction is accepted, then at 10, the push service module 364 notifies the commit service module 366 to commit the protocol(s) into the device 2201. At 11, the commit service module 366 reads the protocol(s) from the staging area 2204. At 12, the commit service module 366 writes the protocol(s) to the protocol database 368. At 13, the commit service module 366 notifies the push service module 364 that the committing is completed. At 14, the push service module 364 notifies the same to the command and notification API 356, which sends the notification to the cloud 2202 side, at 15.

It should be understood that the pushing process described with reference to FIG. 21 and the push data flows described with reference to FIGS. 22A and 22B are for purposes of illustration only and not for limitation. Any suitable process/data flow with more, fewer, and/or different operations can be implemented to push protocols from the cloud to imaging devices.

Thus, certain examples provide protocol management systems and methods including registering devices, pulling protocols from devices to the cloud, organizing protocols/tags in the cloud, standardizing protocols in a library, and pushing protocols back into the device(s) for use. Deviation/change tracking can be viewed to compare what is on the cloud versus what is on the device. Certain examples facilitate protocol organization to define one protocol with an association with multiple scanners and having instructions/parameters that are different for different scanners/devices. Devices can be baselined, and protocol can be standardized, organized, and managed with respect to device content. A user can work from a device view and/or a protocol view to baseline, push/pull, and manage devices, protocols, analytics, etc.

Certain examples facilitate interaction between a cloud-based imaging protocol manager and a cloud agent, the cloud agent serving as intermediary between an imaging device and the imaging protocol manager. The cloud agent provides flexibility to communicate with a plurality of imaging devices including new and legacy devices, installations, and configurations. Using the cloud agent, protocol information can be pulled from and pushed to an imaging device in a format readable and/or otherwise actionable by the imaging device, rather than in a format that must be translated for use by the imaging device. Similarly, certain examples enable the imaging protocol manager to understand, analyze, and update the imaging protocol in a device-usable format.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, including best mode, it will be apparent to those of ordinary skill in the art that numerous modifications, including, but not limited to, form, function, manner of operation and use may be made without departing from the principles and concepts set forth herein in this written description. Also, as used herein, the examples and embodiments, in all respects, are meant to be illustrative only and should not be construed to be limiting in any manner.

What is claimed is:

1. A system comprising:
    one or more processor and one or more storage devices in a cloud; and
    a cloud-based imaging protocol manager leveraging the one or more processors and the one or more storage devices, wherein the imaging protocol manager comprising:
        a library storing standard imaging protocols;
        a compatibility checker configured to determine one or more compatible imaging devices from a plurality of imaging devices registered with the imaging protocol manager that are compatible with one or more standard imaging protocols of the library;
        an orchestrator configured to create a push command which requests pushing the one or more standard imaging protocols to a particular imaging device of the one or more compatible imaging devices;
        a command queue storing the push command, wherein the particular imaging device polls the command queue to receive the push command;
        a push enricher configured to convert the one or more standard imaging protocols to one or more raw protocols in a format used by the particular imaging device;
        a data store storing the one or more raw protocols for the particular imaging device to download; and
        a notification queue storing a notification from the particular imaging device, wherein the notification indicates execution status of the push command.

2. The imaging protocol manager of claim 1, wherein the standard imaging protocols in the library are stored in JavaScript Object Notation (JSON) format.

3. The imaging protocol manager of claim 1, further comprising a web host configured to support a web-based portal or application, wherein the web-based portal or application is accessible by a user via a user device, and the user identifies the one or more standard imaging protocols via the user device.

4. The imaging protocol manager of claim 1, wherein determining the one or more compatible imaging devices comprises:

comparing a model identifier associated with the one or more standard imaging protocols with each model identifier associated with each of the plurality of imaging devices; and identifying the one or more compatible devices that each have a model identifier matching the model identifier associated with the one or more standard imaging protocols.

5. The imaging protocol manager of claim 1, wherein the orchestrator is further configured to log push information including at least some of: the one or more standard imaging protocols, the particular imaging device, a user who requests pushing the one or more standard protocols, a time when the push command is created, a time when the notification is received.

6. An apparatus comprising a processor, and a memory storing instructions when executed by the processor causes the processor to function as a cloud agent in communication with a cloud-based imaging protocol manager to:

poll the imaging protocol manager and receive a push command from a command queue of the imaging protocol manager, wherein the push command requests pushing one or more standard imaging protocols to an imaging device registered with the imaging protocol manager;

download one or more raw protocols associated with the push command from the imaging protocol manager, wherein the one or more raw protocols are converted from the one or more standard imaging protocols by the imaging protocol manager;

notify a user of the push command;

commit or refuse to commit the one or more raw protocols to a protocol database of the imaging device based on a user input; and send a notification indicating execution status of the push command to the imaging protocol manager.

7. The apparatus of claim 6, wherein the apparatus is the imaging device.

8. The apparatus of claim 6, wherein the apparatus is a device or system that facilitates communication between the imaging device and the imaging protocol manager.

9. The apparatus of claim 6, wherein committing or refusing to commit the one or more raw protocols comprises:

receiving the user input via a user interface;

committing the one or more raw protocols in response to the user input indicating acceptance; and refusing to commit the one or more raw protocols in response to the user input indicating rejection.

10. The apparatus of claim 6, wherein the push command is one of the following types: Replace All command that requests replacing all existing raw protocols in the protocol database with the one or more raw protocols, Add New command requests adding the one or more raw protocols to the protocol database, Modify Existing command requests modifying one or more corresponding raw protocols in the protocol database with the one or more raw protocols, Delete command requests deleting the one or more raw protocols from the protocol database.

11. A method performed by an imaging protocol manager in a cloud for pushing imaging protocols from the cloud to imaging devices, the method comprising:

storing standard imaging protocols in the cloud;

determining one or more compatible imaging devices from a plurality of imaging devices registered with the imaging protocol manager that are compatible with one or more standard imaging protocols of the library;

creating a push command which requests pushing the one or more standard imaging protocols to a particular imaging device of the one or more compatible imaging devices;

storing the push command in a command queue, wherein the particular imaging device polls the command queue to receive the push command;

converting the one or more standard imaging protocols to one or more raw protocols in a format used by the particular imaging device;

storing the one or more raw protocols for the particular imaging device to download; and receiving a notification from the particular imaging device, wherein the notification indicates execution status of the push command.

12. The method of claim 11, wherein the standard imaging protocols in the cloud are stored in JavaScript Object Notation (JSON) format.

13. The method of claim 11, further comprising:

receiving a user input from a web-based portal or application supported by the imaging protocol manager, wherein the user input identifies the one or more standard imaging protocols.

14. The method of claim 11, wherein determining the one or more compatible imaging devices comprises:

comparing a model identifier associated with the one or more standard imaging protocols with each model identifier associated with each of the plurality of imaging devices; and identifying the one or more compatible devices that each have a model identifier matching the model identifier associated with the one or more standard imaging protocols.

15. The method of claim 11, further comprising logging push information including at least some of: the one or more standard imaging protocols, the particular imaging device, a user who requests pushing the one or more standard protocols, a time when the push command is created, a time when the notification is received.

16. A method performed by an apparatus, comprising a processor, in communication with an imaging protocol manager in a cloud for pushing imaging protocols from the cloud to an imaging device registered with the imaging protocol manager, the method comprising:

polling the imaging protocol manager and receiving a push command from a command queue of the imaging protocol manager, wherein the push command requests pushing one or more standard imaging protocols to the imaging device;

downloading one or more raw protocols associated with the push command from the imaging protocol manager, wherein the one or more raw imaging protocols are converted from the one or more standard imaging protocols by the imaging protocol manager;

notifying a user of the push command;

committing or refusing to commit the one or more raw protocols to a protocol database of the imaging device based on a user input; and sending a notification indicating execution status of the push command to the imaging protocol manager.

17. The method of claim 16, wherein the apparatus is the imaging device.

18. The method of claim 16, wherein the apparatus is a device or system that facilitates communication between the imaging device and the imaging protocol manager.

19. The method of claim 16, wherein committing or refusing to commit the one or more raw protocols comprises:

receiving the user input via a user interface;

committing the one or more raw protocols in response to the user input indicating acceptance; and refusing to commit the one or more raw protocols in response to the user input indicating rejection.

20. The method of claim 16, wherein the push command is one of the following types: Replace All command that requests replacing all existing raw protocols in the protocol database with the one or more raw protocols, Add New command requests adding the one or more raw protocols to the protocol database, Modify Existing command requests modifying one or more corresponding raw protocols in the protocol database with the one or more raw protocols, Delete command requests deleting the one or more raw protocols from the protocol database.

\* \* \* \* \*